US006723831B2

(12) United States Patent
Duthaler et al.

(10) Patent No.: US 6,723,831 B2
(45) Date of Patent: *Apr. 20, 2004

(54) NEOGLYCOPROTEINS

(75) Inventors: Rudolf Duthaler, Bettingen (CH);
Andreas Katopodis, Oberwil (CH);
Willy Kinzy, Lörrach (DE); Reinhold Öhrlein, Rheinfelden (DE); Gebhard Thoma, Lörrach (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/123,396

(22) Filed: Apr. 16, 2002

(65) Prior Publication Data

US 2002/0164347 A1 Nov. 7, 2002

Related U.S. Application Data

(63) Continuation of application No. 09/403,111, filed as application No. PCT/EP98/02227 on Apr. 16, 1998, now Pat. No. 6,399,071.

(30) Foreign Application Priority Data

Apr. 18, 1997 (EP) .............................................. 97810243
Apr. 18, 1997 (EP) .............................................. 97810244
Feb. 5, 1998 (GB) ................................................ 9802450

(51) Int. Cl.[7] .......................... C07K 1/107; C07K 1/22; C07K 14/00; C07K 16/06
(52) U.S. Cl. ..................... 530/322; 525/54.2; 530/322; 530/345; 530/395; 530/405; 530/411; 536/17.6
(58) Field of Search ............................ 424/193.1, 194.1; 514/2, 8, 25, 54, 61, 62; 525/54.1, 54.2, 54.3; 527/312; 528/271, 332, 360, 363, 364, 422; 530/300, 322, 345, 350, 395, 405, 409, 411; 536/17.6

(56) References Cited

U.S. PATENT DOCUMENTS

| 5,149,425 A | 9/1992 | Mazid ..................... 210/198.2 |
| 6,399,071 B1 * | 6/2002 | Duthaler et al. ......... 424/194.1 |

FOREIGN PATENT DOCUMENTS

| EP | 601 417 A2 | 6/1994 |
| WO | WO 92/22318 | 12/1992 |
| WO | WO 93/03735 | 3/1993 |
| WO | WO 96/15810 | 5/1996 |
| WO | WO 97/19105 | 5/1997 |

OTHER PUBLICATIONS

Moussebois et al. Synthesis of N-Chloroacetyl Derivatives . . . J. Org. Chem. 1976, vol. 41, No. 8, pp. 1340–1343.*
Monsigny M. et al., Advanced Drug Delivery Reviews, vol. 14, pp. 1–24 (1994).
Romanowska A. et al., Methods in Enzymology, vol. 242, pp. 90–101 (1994).
Roy R. et al., J.Chem.Soc.Chem.Commun., pp. 1869–1872 (1993).
Roy R., Trends in Glycoscience and Glycotechnology, vol. 8, No. 40, pp. 79–99 (1996).
Thoma G. et al., J.Am.Chem.Soc., vol. 119 pp. 7414–7415 (1997).

* cited by examiner

*Primary Examiner*—Jeffrey E. Russel
(74) *Attorney, Agent, or Firm*—Gabriel Lopez

(57) ABSTRACT

Polyamide conjugates comprising either (a) a xenoantigenic group; or (b) a biologically active group and a macromolecular, macro- or microscopic entity; bound to a polyamide backbone, processes for their preparation and the use of these conjugates in therapeutic compositions.

11 Claims, No Drawings

NEOGLYCOPROTEINS

This is a continuation of Ser. No. 09/403,111, Oct. 14, 1999, U.S. Pat. No. 6,399,071 B1, which is a 371 of PCT/EP98/02227 Apr. 16, 1998.

The present invention relates to novel polyamide conjugates, processes for their preparation and the use of these conjugates in therapeutic compositions.

The increased shortage of donor organs for transplantation from human to human has led to a great interest in the possibilities of xenotransplantation (transplantation from non-human to human). At present research is focused on easily accessible animals, such as pigs, as the source for organs. However, pig to human xenotransplantation has to over-come a series of obstacles the most immediate and striking of them being hyperacute rejection (HAR). HAR is caused by pre-formed 'natural' polyclonal antibodies which are mostly directed against carbohydrate cell surface epitopes containing terminal Gal α1,3Gal structures (anti-αGal). In addition, other antibodies may also exist directed against N-glycolyl neuraminic acid structures also present on pig endothelium.

To achieve long term graft survival, strategies which address the xenoreactive antibodies are needed. One approach is removal of antibodies by injection of high affinity ligands which may act as inhibitors of antibody deposition on transplanted tissue. Another approach is immunoapheresis, a further development of plasmapheresis, a clinically established procedure similar to dialysis. Immunoapheresis involves the extracorporal treatment of blood by first separating the blood cells, then passage of plasma through immunoaffinity columns, re-mixing of blood cells with the antibody depleted plasma and reintroducing the blood into the patient.

Thus, there is a need for ligands able to bind intracorporally and for a column material able to bind extracorporally the polyclonal xenoreactive antibodies with improved affinity.

The present invention relates to a polyamide conjugate comprising either (a) a xenoantigenic group;

or (b) a biologically active group and a macromolecular, macro- or microscopic entity; bound to a polyamide backbone wherein the polyamide backbone comprises at least one structural element of formula I

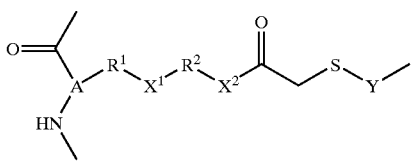

(I)

and in case (b) additionally at least one structural element of formula II

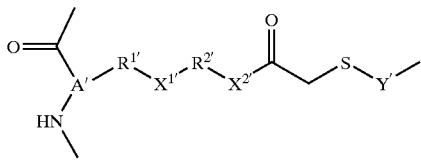

(II)

in which each of A and A', independently, is a trivalent bridging group;

each of $R^1$ and $R^{1'}$, independently, is a direct bond or $C_1$–$C_6$alkylene;

each of $X^1$ and $X^{1'}$, independently, is —C(O)O—, —C(O)NR—, —NR—, —S— or —O—;

each of $R^2$ and $R^{2'}$, independently, is a direct bond or a bivalent bridging group;

each of $X^2$ and $X^{2'}$, independently, is a direct bond or —O— or —NR—; wherein R is hydrogen, OH, $C_1$–$C_{12}$alkyl, $C_2$–$C_{12}$alkenyl, $C_3$–$C_8$cycloalkyl, $C_3$–$C_8$cycloalkenyl, $C_2$–$C_7$heterocycloalkyl, $C_2$–$C_{11}$heterocycloalkenyl, $C_6$- or $C_{10}$aryl, $C_5$–$C_9$heteroaryl, $C_7$–$C_{16}$aralkyl, $C_8$–$C_{16}$aralkenyl with $C_2$–$C_6$alkenylene and $C_6$- or $C_{10}$aryl, or di-$C_6$- or $C_{10}$aryl-$C_1$–$C_6$alkyl; and each of Y and Y', independently, is a direct bond or a bivalent bridging group; with the proviso that $X^1$ or $X^{1'}$ is not —NR—, —S— or —O— when $R^1$ or $R^{1'}$ is a direct bond.

When the polyamide backbone of the invention comprises more than one structural element of formula I or II, these elements may be identical or different. It may be homopolymeric or copolymeric, or copolymeric additionally having comonomer units of e.g. other aminocarboxylic acids. The copolymeric backbones may be block or statistical polymers. When the trivalent bridging group is chiral, the polyamide backbones may homogeneously have the L- or D-configuration or contain structural elements of both configurations, as homogeneous blocks or as statistical mixtures including racemates (1:1 mixtures).

The average sum of structural elements of the polyamide backbone [n] may be in the range of from 10 to 10,000, preferably of from 50 to 1,500, more preferably of from 250 to 1,200, most preferably of from 900 to 1200. Polydispersity may range from 1.001 to 2.0, preferably from 1.1 to 1.5, more preferably from 1.15 to 1.2.

Any alkyl and alkylene radical or moiety may be linear or branched. Preferably alkyl is $C_1$–$C_{18}$alkyl, more preferably $C_1$–$C_4$alkyl, and may be e.g. methyl, ethyl, n- or i-propyl, or n-, i- or t-butyl. Preferably alkenyl may contain 2 to 7 C atoms. Aryl or heteroaryl may be a 5 or 6 membered ring or a bicyclic radical of two fused rings, one or more heteroatoms chosen from the group O—, N— and S-atom being present in the heteroaryl. Examples include phenyl, naphthyl, furanyl, pyrrolyl, etc. Aralkyl preferably has 7 to 12 C atoms and may be phenyl-$C_1$–$C_6$alkyl, e.g. benzyl or phenethyl. An example for aralkenyl is cinnamyl.

A or A' may be a single atom with at least three valences, e.g. C, N or Si; in particular

wherein $R^{aa}$ is H, $C_1$–$C_6$alkyl, $C_2$–$C_6$alkenyl, $C_3$–$C_7$cycloalkyl, phenyl or benzyl.

$R^2$ or $R^{2'}$ as a bivalent bridging group may contain from 1 to 35, preferably from 1 to 20, particularly from 1 to 16 C atoms, e.g. $C_1$–$C_{35}$alkylene, $C_2$–$C_8$alkenylene, $C_2$–$C_8$alkynylene, $C_3$–$C_{12}$cycloalkylene, $C_6$–$C_{10}$arylene or $C_7$–$C_{35}$aralkylene wherein the alkylene, alkenylene and alkynylene radicals or moieties may be interrupted by one or more groups selected from —O—, —S—, —C(O)—, —SO$_2$— and —HN—.

The bridging group $R^2$ or $R^{2'}$ may, for example, conform to formula III

—R$^5$—X$^5$—R$^6$—X$^4$—R$^7$—  (III)

in which
each of $X^5$ and $X^4$, independently, is a direct bond, —O—, —S—, —C(O)—, —C(O)O—, —OC(O)—, —OC(O)O—, —SO$_2$O—, —OSO$_2$—, —OSO$_2$O—, —NH—, —NHC(O)—, —C(O)NH—, —NHC(O)O—, —OC(O)NH—, —NHC(O)NH—, —NHSO$_2$—, —SO$_2$NH—, —NHSO$_2$O—, —OSO$_2$NH— or —NHSO$_2$NH—;
each of $R^5$ and $R^7$, independently, is a direct bond, $C_1$–$C_{20}$alkylene, $C_5$- or $C_6$-cycloalkylene, $C_6$–$C_{10}$arylene or $C_7$–$C_{12}$aralkylene; and
$R^6$ is a direct bond or $C_1$–$C_{20}$alkylene which is optionally interrupted by one or more, preferably 2 O atoms;
with the proviso that when $R^6$ is a direct bond $X^4$ is also a direct bond.

Preferably $R^2$ or $R^{2'}$ may be oxyalkylene or polyoxyalkylene, more preferably having from 2 to 4 C atoms, particularly 2 or 3 C atoms, in the alkylene and from 2 to 20, preferably from 2 to 10, alkylene units, especially oxypropylene and polyoxypropylene, e.g. polyoxypropylene having from 2 to 20 preferably from 2 to 10, oxypropylene units.

A polyamide conjugate comprising a xenoantigenic group and no macromolecular, macro- or microscopic entity will hereinafter be referred to as "conjugate Type I" and a polyamide conjugate comprising a biologically active group and a macromolecular, macro- or micro-scopic entity will hereinafter be referred to as "conjugate Type II".

In conjugates Type I the xenoantigenic group is conjugated to the polyamide backbone via Y of a structural element of formula I. The conjugates Type I may comprise one or more identical or different xenoantigenic groups.

A xenoantigenic group may be any group identifiable by known methods, e.g. as disclosed in U.S. Pat. No. 5,695,759 (the contents thereof with respect to the method being incorporated herein by reference), comprising isolating xenoantibodies from human blood by perfusing the blood over xenograft material, e.g. removing bound antibodies from the xenograft and using those antibodies to screen candidate epitopes, e.g. by a suitable immunoassay.

The xenoantigenic group may preferably be derived from an oligosaccharide terminating with an α-linked D-galactopyranose or N-glycoyl-neuraminic acid at its reducing end.

Typically (and with respect to conjugates Type I and II) the oligosaccharide may consist of from 1 to 20, preferably 1 to 15, particularly 1 to 10 sugar monomers selected from naturally occurring and modified sugar monomers. The skilled person is familiar with naturally occurring and modified sugar monomers and oligosaccharides comprising these sugar monomers from the standard works of organic chemistry or biochemistry, for example the Specialist Periodical Reports edited at the beginning by The Chemical Society and now by The Royal Society of Chemistry London, e.g. Ferrier et al. Carbohydrate Chemistry 29 The Royal Society of Chemistry London (1997).

Examples of sugar monomers include D- and L-aldopyranoses and D- and L-aldofuranoses, for example glyceraldehyde, erythrose, threose, ribose, arabinose, xylose, lyxose, allose, altrose, glucose, mannose, gulose, idose, galactose and talose, D- and L-ketopyranoses and D- and L-ketofuranoses, for example dihydroxyacetone, erythrulose, ribulose, xylulose, psicose, fructose, sorbose and tagatose, and also D- and L-diketopyranoses, for example pentodiulose and hexodiulose.

The term sugar monomers also includes those sugar monomers which are modifications of the examples listed, for example, protected, partially protected or unprotected deoxysugars of the D- and L-configurations, preferably 2-, 3-, 4-, 5- and 6-deoxyaldoses, such as fucose, rhamnose and digitoxose, 1,2-dideoxyaldoses, such as glucal, galactal and fucal, and 1-, 3-, 4-, 5- and 6-deoxyketoses, 2-, 3-, 4-, 5- and 6-deoxyaminosugars of the D and L configurations, such as glucosamine, mannosamine, galactosamine and fucosamine, and deoxyacylaminosugars, such as N-acylglucosamine, N-acylmannosamine, N-acylgalactosamine and N-acylfucosamine, preferably their $C_1$–$C_4$alkyl esters. In addition, these modifications are understood to mean aldonic, aldaric and uronic acids, such as gluconic acid or glucuronic acid, and also ascorbic acid and amino acid-carrying sugar monomers. Modified sugar monomers are also understood to mean those having a carbon chain which is longer than 6 C atoms, such as heptoses, octoses, nonoses, heptuloses, octuloses and nonuloses, and also their representatives which are substituted in accordance with the above-listed criteria, such as ketodeoxyoctanic acid, ketodeoxynonanic acid, N-acylneuraminic acids and N-acylmuraminic acids.

If two, three, four or five of the abovementioned, identical or different monomers are assembled the resulting saccharides are denoted as di-, tri-, tetra- or pentasaccharides. The linkage is preferably α-O-glycosidic or β-O-glycosidic, e.g. (1→2)-, (1→3)-, (1→4)-, (1→5)-, (1→6)-, (2→3)- and (2→6)-glycosidic linkages. Examples of disaccharides are e.g. trehalose, sophorose, kojibiose, laminaribiose, maltose, cellobiose, isomaltose, gentibiose, sucrose and lactose, and their derivatives. Examples of trisaccharides are raffinose and melezitose. Furthermore, the oligosaccharides may be linked via S-, N- and C-glycosidic linkages, e.g. —S—, —NR$^{12}$—, —NR$^{12}$C(O)— or —CR$^{13}$R$^{14}$—, wherein R$^{12}$, R$^{13}$ and R$^{14}$ independently of each other are H, $C_1$–$C_{12}$alkyl, $C_5$- or $C_6$cycloalkyl, $C_5$- or $C_6$cycloalkylmethyl or -ethyl, phenyl, benzyl or phenethyl.

In conjugates Type I the following significances are preferred either individually or in any combination or sub-combination:

(a) A is $C_1$–$C_6$alkanetriyl, more preferably methanetriyl.
(b) $R^1$ is $C_1$–$C_6$alkylene, more preferably —(CH$_2$)$_4$—;
(c) $X^1$ is —NR— wherein R has the meanings mentioned above, more preferably $X^1$ is —NH—;
(d) $R^2$ is a direct bond;
(e) $X^2$ is a direct bond;
(f) Y is a group of formula III wherein $R^5$ is $C_1$–$C_8$alkylene, $X^5$ is —NH—, $R^6$ is a direct bond, $X^4$ is —C(O)—, and $R^7$ is $C_1$–$C_8$alkylene, preferably Y is a group of formula IIIa

—(CH$_2$)$_m$NHC(O)(CH$_2$)$_3$—  (IIIa)

wherein m is a number from 1 to 8, preferably 1 to 6; and wherein with respect to formula I —(CH$_2$)$_3$— is bound to S;

(g) the xenoantigenic group, hereinafter referred to as $R^{3a}$, is a group of formula IVa1, IVb1, IVc1, IVd1 or IVe1

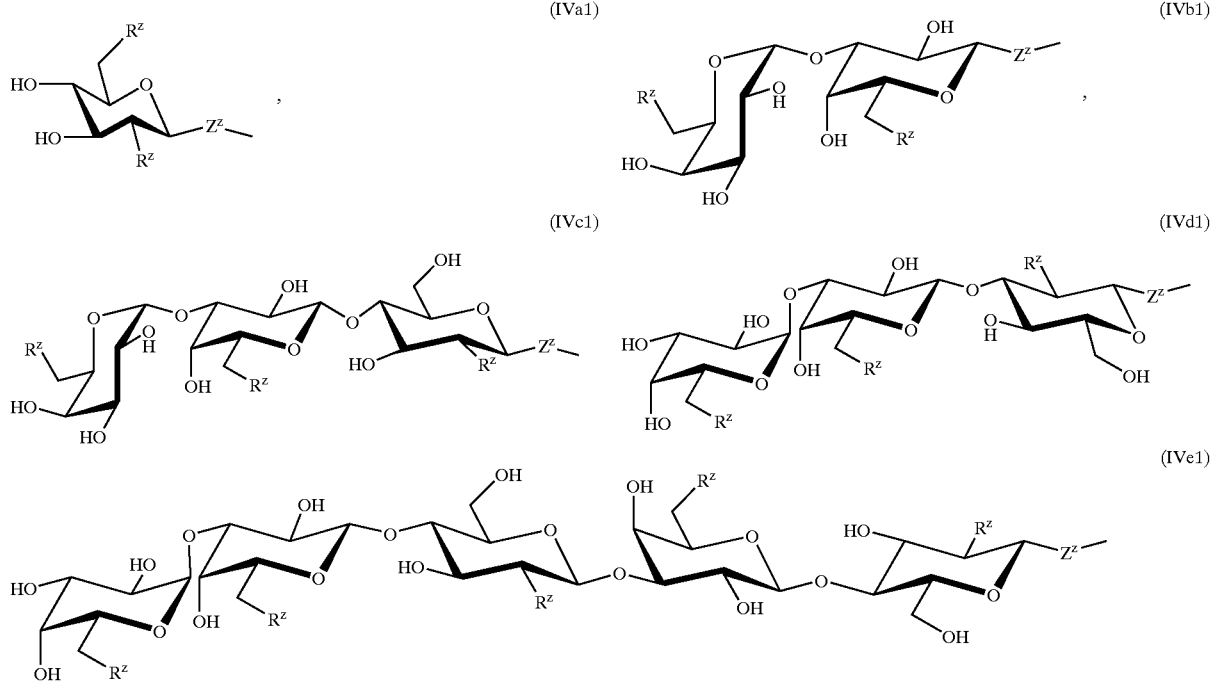

wherein the individual $R^z$ are independently $OR^{z1}$, $SR^{z1}$ or $NHX^zR^{z1}$ wherein $X^z$ is —C(O)—, —C(S)—, —S(O)$_2$—, —C(O)Y— or —C(S)Y—, in which Y is —NH—, —O—, —S—, —S—$C_1$–$C_6$alklene, —NH—$C_1$–$C_6$alkylene, —O—$C_1$–$C_6$alkylene, —$C_1$–$C_6$alkylene-O—, —$C_1$–$C_6$salkylene-S—, —$C_1$–$C_5$alkylene-NH—, —$C_1$–$C_6$alkylene-O—C(O)O—, —$C_1$–$C_6$alkylene-S—C(O)O— or —$C_1$–$C_6$alkylene-NH—C(O)O— and $R^{z1}$ is hydrogen, $C_1$–$C_{20}$alkyl, $C_2$–$C_{20}$alkenyl, $C_3$–$C_{15}$cycloalkyl, $C_3$–$C_{15}$cycloalkenyl, $C_6$–$C_{10}$aryl, $C_7$–$C_{20}$aralkyl or $C_2$–$C_9$heteroaryl, where alkyl, alkenyl, cycloalkyl, cycloalkenyl, aryl, aralkyl and heteroaryl are unsubstituted or substituted by one or more substituents selected from OH, halogen, halo-$C_1$–$C_{20}$alkyl, nitro, $C_1$–$C_{18}$alkyl, $C_1$–$C_8$alkoxy, $C_1$–$C_8$alkenyloxy, amino, mono-$C_1$–$C_{18}$alkylamino, di-$C_1$–$C_{18}$alkylamino, benzylamino, SO$_3$H, SH, thio-$C_1$–$C_{18}$alkyl and NHC(O)—$C_1$–$C_{18}$alkyl; and $Z^z$ is —O— or —NHC(O)—;

preferably a group of formula IVa, IVb, IVc, IVd, IVe or IVf

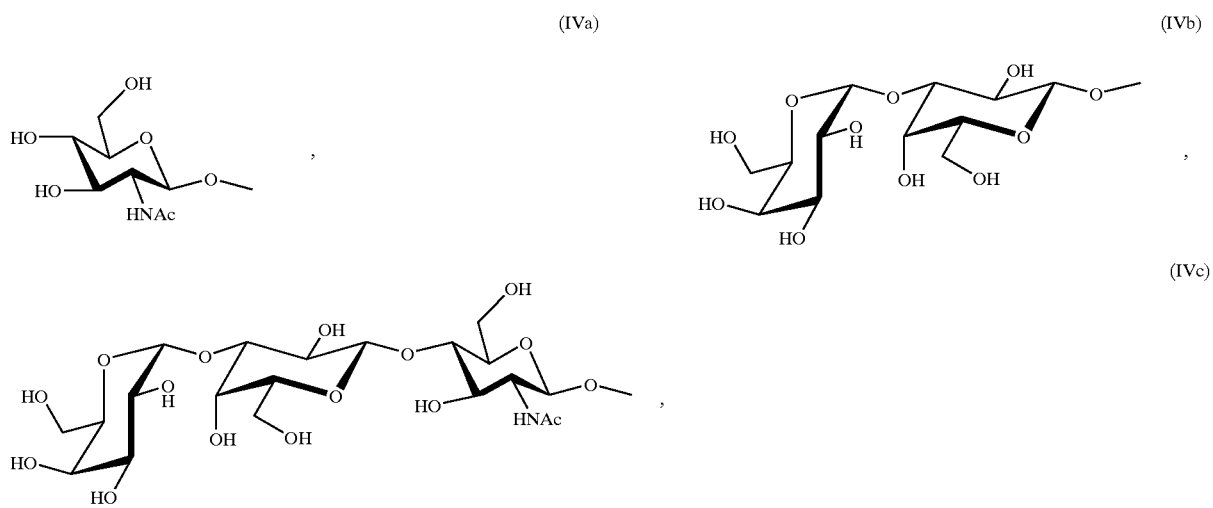

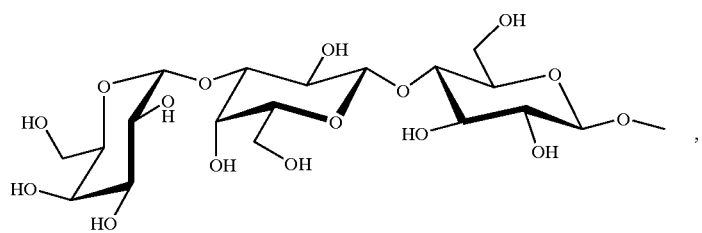
(IVd)
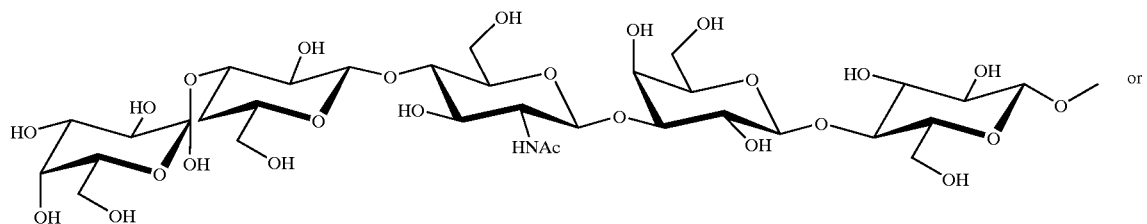
(IVe)
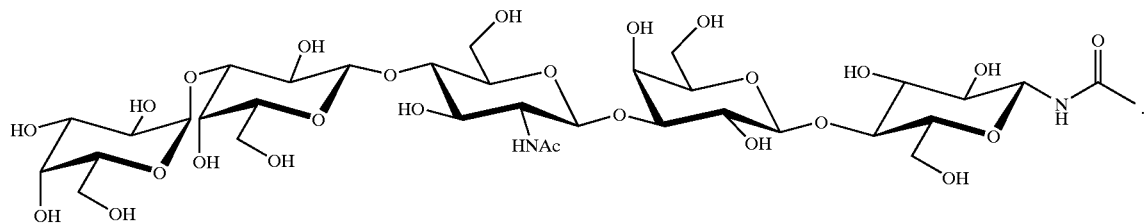
(IVf)
Particularly preferred are conjugates Type I wherein R³ᵃ—Y— is a group of formula Va, Vb, Vc, Vd, Ve or Vf
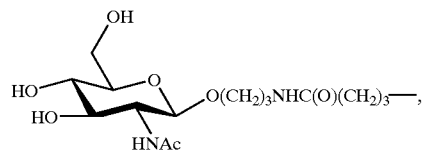
(Va)
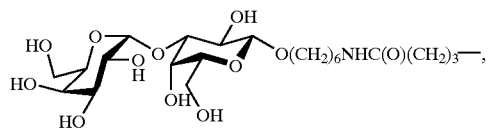
(Vb)
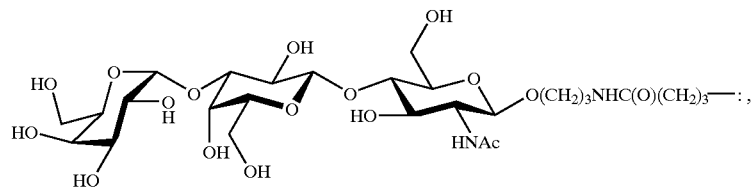
(Vc)
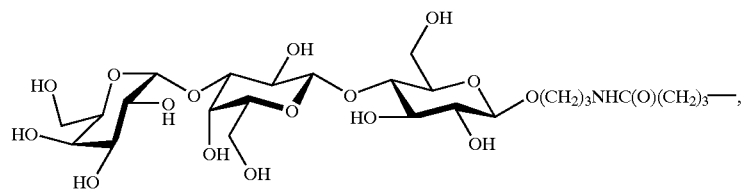
(Vd)
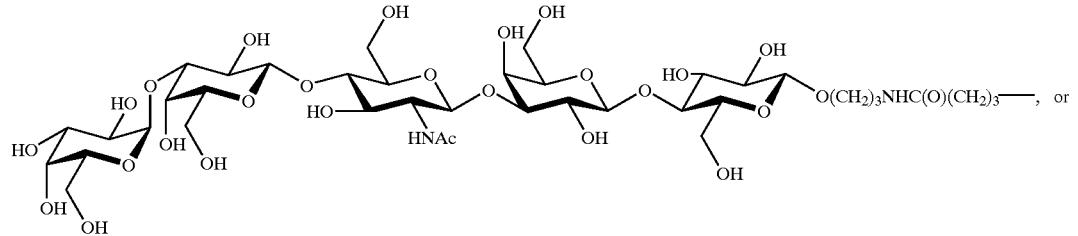
(Ve)

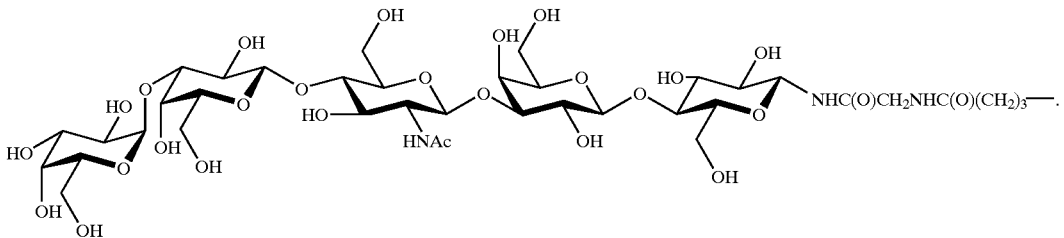

(Vf)

A preferred subgroup are conjugates Type I comprising at least one structural element of formula I*

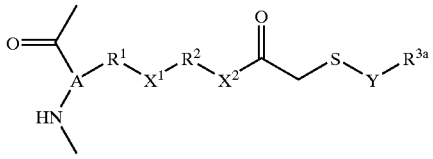

(I*)

wherein
A, $R^1$, $X^1$, $R^2$, $X^2$ and Y are as defined above and $R^{3a}$ is a xenoantigenic group, more preferred a structural element of formula Ia1a, most preferred a structural element of formula Iaa,

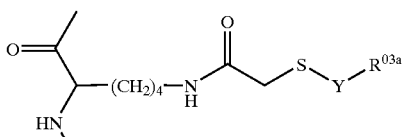

(Ia1a)

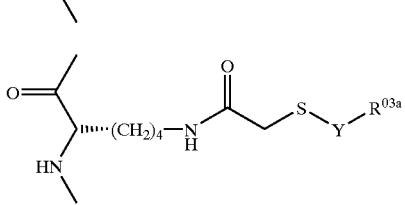

(Iaa)

in which Y is a group of formula IIIa and $R^{03a}$ is a group of formula IVa, IVb, IVc, IVd, IVe or IVf.

Particularly preferred are conjugates Type I comprising at least one structural element of formula Iaa wherein —Y—$R^{03a}$ is a group of formula Va, Vb, Vc, Vd, Ve or Vf.

According to the invention the polyamide backbone of conjugates Type I may additionally comprise at least one structural element of formula VI,

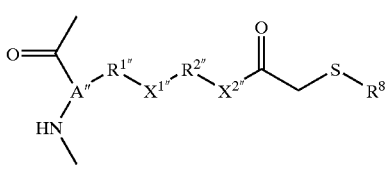

(VI)

in which
A″, $R^{1″}$, $X^{1″}$, $R^{2″}$ and $X^{2″}$ independently have the meanings and preferences as defined for A, $R^1$, $X^1$, $R^2$ and $X^2$, respectively, above and
$R^8$ is a polar group, preferably polyhydroxy-$C_2$–$C_{12}$alkyl or —$C_3$–$C_{12}$cycloalkyl, more preferably polyhydroxy-$C_2$–$C_6$alkyl or —$C_3$–$C_6$cycloalkyl, with 1 to 6, preferably 2 to 5 hydroxy groups, most preferably —$CH_2CHOHCH_2OH$.

A preferred subgroup of structural elements of formula VI are those of formula VIa

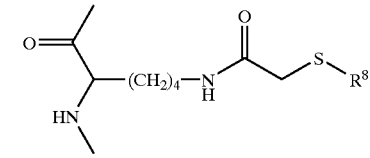

(VIa)

wherein $R^8$ is as defined above.

Particularly preferred structural elements of formula VI are those of formula VIb1

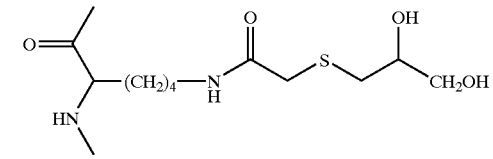

(VIb1)

more preferred those of formula VIb

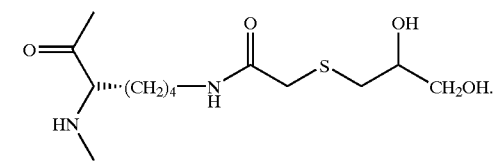

(VIb)

Particularly preferred are conjugates Type I comprising at least one structural element of formula I* and at least one structural element of formula VI wherein A, A″, $R^1$, $R^{1″}$, $X^1$, $X^{1″}$, $R^2$, $R^{2″}$, $X^2$, $X^{2″}$, Y, $R^{3a}$ and $R^8$ have the meanings and preferences as mentioned above.

Most preferred are conjugates Type I comprising at least one structural element of formula Iaa wherein —Y—$R^{03a}$ is a group of formula Va, Vb, Vc, Vd, Ve or Vf and at least one structural element of formula VIb.

In the novel conjugates Type I the content of the structural elements of formulae I* and VI may for example be from 0.1 to 99.9 mol %, the values adding up to 100% in the case of conjugates Type I only consisting of structural elements of formula I* and VI. In the case of structural elements of formula I* the content may for example be from 1 to 50%, preferably from 10 to 30%. In the case of structural elements of formula VI the content may be from 0 to 99%, preferably from 70 to 90%.

Preferred conjugates Type I are those wherein the average sum of structural elements [n] is in the range of from 200 to 300 with a polydispersity of from 1.1 to 1.2 and the ratio of structural elements of formula Iaa [x] is 5 to 30% or those wherein [n] is in the range of from 900 to 1200 with a polydispersity of from 1.1 to 1.2 and [x] is 5 to 50%; with a ratio of structural elements of formula VIb [z] ranging from 45 to 94%; $R^{03a}$—Y— being identical or different and selected from groups of formula Va, Vb, Vc, Vd, Ve and Vf.

Examples of preferred conjugates Type I are those wherein
(a) n is 250, [x] is 25% when $R^{3a}$—Y— is a group of formula Vb; +75% [z];
(b) n is 250, [x] is 8% when $R^{3a}$—Y— is a group of formula Vc; +92% [z];
(c) n is 250, [x] is 16% when $R^{3a}$—Y— is a group of formula Vc; +84% [z];
(d) n is 250, [x] is 41% when $R^{3a}$—Y— is a group of formula Vc; +59% [z];
(e) n is 250, [x] is 61% when $R^{3a}$—Y— is a group of formula Vc; +39% [z];
(f) n is 250, [x] is 23% when $R^{3a}$—Y— is a group of formula Vd; +77% [z];
(g) n is 250, [x] is 22% when $R^{3a}$—Y— is a group of formula Vf; +78% [z];
(h) n is 1000, [x] is 24% when $R^{3a}$—Y— is a group of formula Vc; +76% [z];
(i) n is 1050, [x] is 21% when $R^{3a}$—Y— is a group of formula Vb; +79% [z];
(j) n is 1050, [x] is 28% when $R^{3a}$—Y— is a group of formula Vc; +72% [z];
(k) n is 1050, [x] is 25% when $R^{3a}$—Y— is a group of formula Vf; +75% [z]; and
(l) n is 1050, [x] is 27% when $R^{3a}$—Y— in a third of structural elements of formula I* is a group of formula Vb, in another third is a group of formula Vc and in another third is a group of formula Vf; +73% [z];
particularly examples (i) to (l).

The novel conjugates Type I are obtainable by a process comprising reacting a polyamide comprising at least one structural element of formula VII

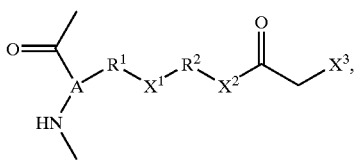

(VII)

in which A, $R^1$, $X^1$, $R^2$ and $X^2$ are as defined above and $X^3$ is halogen, obtainable e.g. as disclosed in WO 97/19105, with a thiol of formula VIIIa'

$$R^{3a}\text{—Y—SH} \qquad (VIIIa'),$$

in which $R^{3a}$ and Y are as defined above.

The thiols are either known or may be prepared in accordance with known methods, e.g. by reacting an amino-functionalized xenoantigen, e.g. the oligosaccharide, with a thiolactone.

When the xenoantigen is a saccharide it may be prepared according to conventional chemical procedures, using enzymes or by following a mixed approach. The use of enzymes for the preparation of oligosaccharide derivatives is disclosed e.g. in WO 97/28173 and WO 97/128174.

Conjugates Type I additionally comprising at least one structural element of formula VI are obtainable by a process comprising reacting a polyamide comprising at least two structural elements of formula VII, with one or more compounds selected from the group of a thiol of formula VIIIa' and a thiol of formula IX $$R^8\text{—SH} \qquad (IX)$$

in which $R^8$ is as defined above.

Preferably the reaction may be carried out in the presence of a strong, non-nucleophilic base, preferably an organic base having at least one tertiary N atom; particularly bicyclic or polycyclic amines. Examples are quinuclidine and 1,8-diazabicyclo[5.4.0]undec-7-ene(1,5-5) (DBU). The base may be employed in at least equimolar quantities, preferably in slight excesses.

The reaction may also be carried out using alkali metal thiolates $R^{3a}$SM wherein M is an alkali metal, for example Li or Na.

A polar, aprotic solvent, preferably a nitrogen-dialkylated carboxyimide, lactam, sulfoxide or sulfone, for example dimethylformamide, may be used. The reaction may be effected either without or with the addition of water, for example up to quantities at which the polymer remains in solution. Non-limiting details for the preparation of the conjugates Type I are disclosed in Examples A through C1.

The novel conjugates Type I have interesting properties. In particular they have affinity for human polyclonal xenoreactive antibodies present in body fluids, e.g. blood, and are useful as ligands or depleting agents. Preferably the conjugates Type I are used for intracorporal depletion of xenoantibodies, comprising administering, e.g. by injection, infusion or perfusion, into a xenograft recipient prior to and/or after transplantation of the xenograft a conjugate Type I. The dosage may be from 0.0001 to 10, preferably from 0.01 to 5, more preferably from 0.2 to 2 mg per kg bodyweight per injection. The administration may be repeated as required prior to transplantation and/or after transplantation as long as removal of antibodies is of therapeutic benefit.

The novel conjugates Type I may also be used as a pharmaceutical for inducing tolerance or anergy towards the xenoantigenic epitopes or to specifically target B cells with xenoantigen receptors. When administered, e.g. by injection, into a xenograft recipient prior to transplantation of the xenograft the dosage of a conjugate Type I may be from 0.0001 to 10, preferably from 0.001 to 5, more preferably from 0.02 to 2 mg per kg bodyweight per injection. The administration may be repeated as required to achieve tolerance.

The conjugates Type I may be administered as a single conjugate or as a mixture of different conjugates Type I as such or in the form of a composition adapted for intravenous administration, e.g. together with one or more pharmaceutically acceptable carrier or diluent therefor. Such mixture may comprise conjugates Type I differing with respect to the polyamide backbone and/or to xenoantigenic group.

Preferred are compositions wherein the conjugate Type I comprises identical or different xenoantigenic groups or compositions comprising a mixture of conjugates Type I, each conjugate comprising identical or different xenoantigenic groups, the xenoantigenic groups being derived from a disaccharide, preferably a group of formula IVb, from a trisaccharide, preferably a group of formula IVc or IVd, or from a pentasaccharide, preferably a group of formula IVe or IVf. Preferably the composition may comprise a conjugate Type I comprising a group derived from a disaccharide, a group derived from a trisaccharide and a group derived from a pentasaccharide, in a ratio of from 5 to 0.1:5 to 0.1:5 to 0.1, preferably in a ratio of 1:1:1 or a mixture of conjugates Type I each conjugate comprising identical xenoantigenic groups, the xenoantigenic groups being derived from a disaccharide, a trisaccharide or a pentasaccharide, the conjugates being present in the composition in a ratio of from 5 to 0.1:5 to 0.1:5 to 0.1, preferably in a ratio of 1:1:1.

In accordance with the foregoing the present invention further provides:

(a) a conjugate Type I for use as a pharmaceutical, preferably as an agent for removing xenoantibodies from human body fluid or as a ligand to present xeno-antigen in the induction of tolerance or anergy;

(b) a method for removing xenoantigenic antibodies from a xenograft recipient, which method comprises intracorporally contacting said body fluid with a conjugate Type I as under (a);

(c) a method for inducing tolerance or anergy towards the xenoantigenic epitopes or to specifically target B cells with xenoantigen receptors in a subject in need of such treatment, which method comprises administering, e.g. by injection, infusion or perfusion, into a xenograft recipient prior to and/or after transplantation of the xenograft an effective amount of a conjugate Type I as under (a);

(d) a composition comprising a conjugate Type I as under (a) or a mixture of such conjugates Type I as hereinbefore disclosed for use preferably in a method for removing xenoantibodies from human body fluid or for inducing tolerance or anergy towards the xenoantigenic epitopes or to specifically target B cells with xenoantigen receptors.

In conjugates Type II the biologically active group is conjugated to the polyamide backbone via Y of a structural element of formula I and the macromolecular, macro- or microscopic entity is conjugated to the polyamide backbone via Y' of a structural element of formula II. The conjugates Type II may comprise one or more identical or different biologically active groups. The conjugates Type II may comprise one or more identical or different macromolecular, macro- or microscopic entities. A single entity may be bound to one or simultaneously to 2 or more structural elements from the same polyamide backbone. Alternatively a single entity may simultaneously be bound to one or more structural elements from different polyamide backbones.

Examples for a biologically active group are radicals derived from alkaloids, carbohydrates, vitamins, peptides, proteins, conjugated proteins, lipids, terpenes, oligonucleotides, antigens and antibodies; or any other ligand, which is preferably recognised in a multivalent form by its receptor or a cellular surface. Preferably the biologically active group is derived from an antigen, preferably from a xenoantigen, more preferred from an oligosaccharide terminating with an α-linked D-galactopyranose or N-glycoyl-neuraminic acid at the reducing end, e.g. as hereinbefore described for the conjugates Type I.

Examples for macromolecular, micro- and macroscopic entities are globular proteins such as serum albumin or KLH; polymers such as poly-amides, poly-imides, poly-ethylene glycols, poly-styrenes, poly-acrylates, poly-acrylamides, co- and block-polymers thereof, natural and modified polysaccharides; glass beads, silica gel, diatomeous earth and structures formed from aggregated or crosslinked lipid mono- or bi-layers, or multiple bilayers. If the macromolecular, micro- or macroscopic entity is a polysaccharide it may consist of more than 20 sugar monomers with a molecular weight of from a few thousand to as high as 100 million. The skilled person is familiar with natural and modified polysaccharides which differ in the nature of their recurring monosaccharide units, in the length of their chains, and in the degree of branching. Modified natural polysaccharides may comprise derivatives obtainable by reacting natural polysaccharides with mono-, bi- or polyfunctional reagents or oxidants, which may substantially be based on modifications of the hydroxy groups of the polysaccharides by ether or ester forming reactions or selective oxidations. Particularly useful are cross-linked, preferably three-dimensionally linked polysaccharides. Examples for natural and modified polysaccharides are natural and modified starches, celluloses, dextrans and agaroses. Particularly useful as cross-linked, preferably three-dimensionally linked polysaccharides are e.g. Sephacryl® and Sepharose® and their derivatives, e.g. NHS-activated CH-Sepharose 4B or NHS-activated Sepharose 4 Fast Flow (commercially available).

In conjugates Type II each of A, A', $R^1$, $R^{1'}$, $X^1$, $X^{1'}$, $R^2$, $R^{2'}$, $X^2$ and $X^{2'}$, independently, has one of the preferred significances given above for the conjugates Type I either individually or in any combination or sub-combination, including:

(g) Y' is a group of formula III wherein $R^5$ is a direct bond, $X^5$ is —NH—, $R^6$ is —[(CH$_2$)$_2$O]$_2$(CH$_2$)$_2$—, $X^4$ is —NHC(O)—, and $R^7$ is $C_1$–$C_8$alkylene, preferably Y' is a group of formula IIIb

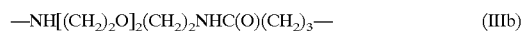

—NH[(CH$_2$)$_2$O]$_2$(CH$_2$)$_2$NHC(O)(CH$_2$)$_3$— (IIIb)

wherein with respect to formula II —(CH$_2$)$_3$— is bound to S;

(h) the biologically active group, hereinafter referred to as $R^3$, is a group of formula IVa1, IVb1, IVc1, IVd1 or IVe1 as above, preferably a group of formula IVa, IVb, IVc, IVd, IVe or IVf as above;

(i) the macromolecular, macro- or microscopic entity, hereinafter referred to as $R^4$, is preferably derived from a natural or modified polysaccharide, more preferably from cellulose, agarose or sepharose, particularly from NHS-activated CH-Sepharose 4B or NHS-activated Sepharose 4 Fast Flow, most preferably from NHS-activated Sepharose 4 Fast Flow.

Particularly preferred are conjugates Type II wherein $R^3$—Y— is a group of formula Va, Vb, Vc, Vd, Ve or Vf as above.

A preferred subgroup are conjugates Type II comprising at least one structural element of formula I**

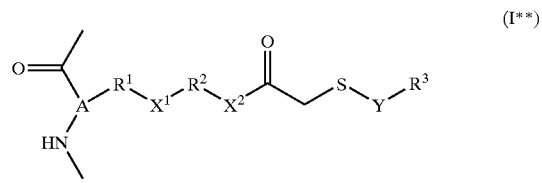

(I**)

wherein

A, $R^1$, $X^1$, $R^2$, $X^2$ and Y are as defined above and $R^3$ is a biologically active group, more preferred a structural element of formula Ia1, (Ia1)

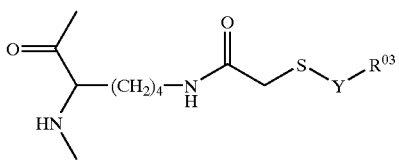

most preferred a structural element of formula Ia, (Ia)

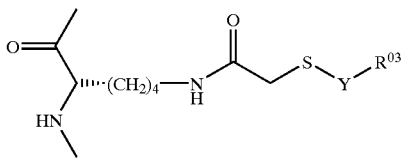

in which Y is a group of formula IIIa and $R^{03}$ is a group of formula IVa, IVb, IVc, IVd, IVe or IVf.

Particularly preferred are conjugates Type II comprising at least one structural element of formula Ia wherein —Y—$R^{03}$ is a group of formula Va, Vb, Vc, Vd, Ve or Vf.

Particularly preferred are conjugates Type II wherein $R^4$—Y'— is a group of formula Vg (Vg)

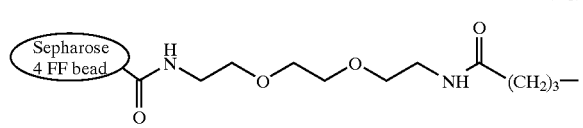

A preferred subgroup are conjugates Type II comprising at least one structural element of formula II*

(II*)

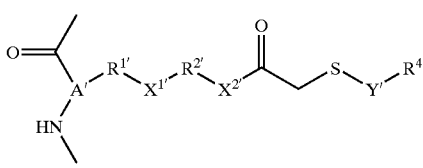

wherein

A, $R^1$, $X^1$, $R^2$, $X^2$ and Y are as defined above and $R^4$ is a macromolecular, macro- or microscopic entity, more preferred a structural element of formula IIa1, (IIa1)

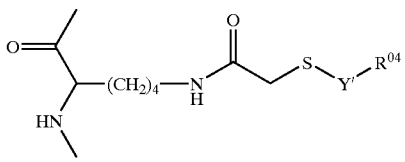

most preferred a structural element of formula IIa, (IIa)

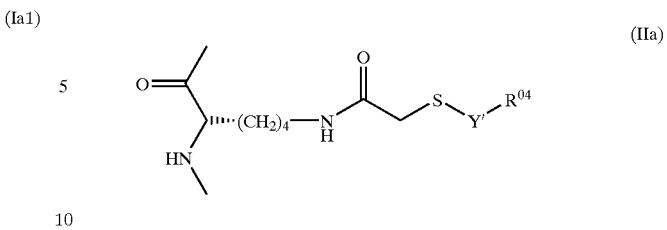

in which —Y'—$R^{04}$ is a group of formula Vg.

According to the invention the polyamide backbone of conjugates Type II may additionally comprise at least one structural element of formula VI with all the meanings and preferences as above.

Particularly preferred are conjugates Type II comprising at least one structural element of formula I**, at least one structural element of formula II* and at least one structural element of formula VI wherein A, A', A", $R^1$, $R^{1'}$, $R^{1''}$, $X^1$, $X^{1'}$, $X^{1''}$, $R^2$, $R^{2'}$, $R^{2''}$, $X^2$, $X^{2'}$, $X^{2''}$, Y, Y', $R^3$, $R^4$ and $R^8$ have the meanings and preferences as mentioned above.

Most preferred are conjugates Type II comprising at least one structural element of formula Ia wherein —Y—$R^{03}$ is a group of formula Va, Vb, Vc, Vd, Ve or Vf, at least one structural element of formula IIa and at least one structural element of formula VIb.

In the novel conjugates Type II the content of the structural elements of formulae I**, II* and VI may for example be from 0.1 to 99.9 mol %, the values adding up to 100% in the case of conjugates Type II only consisting of structural elements of formulae I**, II* and VI. In the case of structural elements of formula I** the content may for example be from 1 to 50%, preferably from 10 to 30%. In the case of structural elements of formula II* the content may for example be from 0.1 to 20%, preferably from 0.1 to 5%. In the case of structural elements of formula VI the content may be from 0 to 98.9%, preferably from 50 to 98.9%. Examples for useful ratios are disclosed in the following table:

| element 1** [%] | 25 | 13 | 14 | 23 | 20 | 21.5 | 16 | 12.5 | 16 |
|---|---|---|---|---|---|---|---|---|---|
| element 11* [%] | 2 | 2.6 | 2.6 | 3 | 3 | 2 | 2.5 | 2.5 | 2.5 |

Preferred conjugates Type II are those wherein the average sum of structural elements [n] is in the range of from 200 to 300 with a polydispersity of from 1.1 to 1.2, the ratio of structural elements of formula Ia [x] wherein $R^{03}$—Y— is a group selected from a group consisting of groups of formula Va, Vb, Vc, Vd, Ve and Vf is 5 to 30% and the ratio of structural elements of formula IIb (intermediate to structural element of formula IIa, see below) [y]

(IIb)

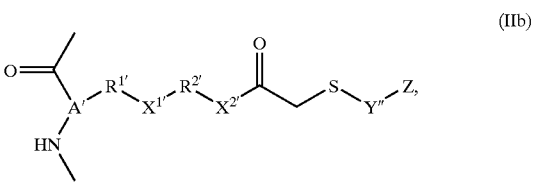

wherein Z—Y" is $H_2N[(CH_2)_2O](CH_2)_2NHC(O)(CH_2)_3$— is from 1 to 5%;

or those wherein [n] is in the range of from 900 to 1200 with a polydispersity of from 1.1 to 1.2, [x] is 5 to 50% and [y] is from 1 to 5%;

with a ratio of structural elements of formula VIb [z] ranging from 45 to 94%.

Examples of preferred conjugates Type II are those wherein
(a) n is 250, x is 25% when $R^3$—Y— is a group of formula Vc and y is 2%; +73% [z];
(b) n is 250, x is 14% when $R^3$—Y— is a group of formula Vc and y is 2.6%; +83.4% [z];
(c) n is 250, x is 21.5% when $R^3$—Y— is a group of formula Va and y is 2%; +76.5% [z];
(d) n is 1050, x is 13% when $R^3$—Y— is a group of formula Vc and y is 2.6%; +84.4% [z];
(e) n is 1050, x is 16% when $R^3$—Y— is a group of formula Vb and y is 2.5%; +81.5% [z];
(f) n is 1050, x is 12.5% when $R^3$—Y— is a group of formula Vf and y is 2.5%; +85% [z]; or
(g) n is 1050, x is 16% when $R^3$—Y— is a group of formula Ve and y is 2.5%; plus 81.5% [z];
particularly examples (d) to (g).

The novel conjugates Type II are obtainable by a process comprising reacting a polyamide comprising at least two structural elements of formula VII as above with one or more compounds or entities selected from the group of a thiol of formula VIII

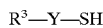
$R^3$—Y—SH    (VIII), in which $R^3$ and Y are as defined above,
a thiol of formula VIIIa

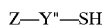
Z—Y"—SH    (VIIIa)

wherein Y" is a bridging group of formula III wherein $R^5$ is a direct bond and the other meanings are as defined above, and Z is hydrogen or a protecting group for $X^4$, preferably an amino protecting group,
and an appropriately derivatized macromolecular, macro- or microscopic entity.

Polyamide conjugates comprising a structural element resulting from the reaction of a structural element of formula VII with a thiol of formula VIIIa may, after elimination of the protecting group Z, conveniently be further reacted with a thiol of formula VIII or an appropriately derivatized macromolecular, macro- or microscopic entity.

The term "appropriately derivatized macromolecular, macro- or microscopic entity" is to be understood as denoting a macromolecular, macro- or microscopic entity carrying at least one functional group suitable to react with a structural element of formula IIb. Examples for functional groups useful for coupling of large entities are known to the skilled artisan and described e.g. in Gabius and Gabius (Eds.) Lectins and Cancer 53ff, Springer Verlag, Berlin Heidelberg (1991). Examples are amine/activated carboxylate (N-hydroxy-succinimidyl ester, pentafluorophenyl ester), amine/epoxide, amine/isocyanate, amine/isothiocyanate, amine Michael-acceptor (maleimide), thiol/thiophil and amine/aldehyde.

The derivatized macromolecular, macro- or microscopic entity may be prepared by reacting a macromolecular, macro- or microscopic entity with known bifunctional linkers.

The thiols of formulae VIII and VIIIa may be obtained as disclosed above for the thiols of formula VIIIa'.

Conjugates Type II additionally comprising a structural element of formula VI are obtainable by a process comprising reacting a polyamide comprising at least three structural elements of formula VII, with one or more compounds or entities selected from the thiols of formulae VIII and VIIIa, an appropriately derivatized macromolecular, macro- or microscopic entity and a thiol of formula IX as above. In particular the process may comprise reacting a polyamide comprising at least three structural elements of formula VII, with one or more compounds or entities selected from the thiols of formulae VIII, VIIIa and IX as above, eliminating the protecting group Z and further reacting the resulting compound with an appropriately derivatized macromolecular, macro- or microscopic entity.

Reaction conditions may be in accordance with the reaction conditions as described for conjugates Type I above.

Non-limiting details for the preparation of the conjugates Type II are disclosed in Examples A through D.

The novel conjugates Type II have interesting properties. In particular they have affinity for human polyclonal xenoreactive antibodies and are useful as adsorbent in the affinity chromatography of body fluids. Preferably the body fluid is blood, particularly blood plasma.

Preferably the conjugates Type II are used for extracorporal removal of antibodies from a body fluid, comprising withdrawing antibody-containing body fluid from a xenograft recipient prior to and/or after transplantation of the xenograft, removing preformed antibodies from the fluid via affinity chromatography comprising the conjugates Type II as adsorbent, and reintroducing the antibody-depleted body fluid into the recipient.

The affinity chromatography may preferably be performed as column chromatography wherein the column is packed with conjugate Type II in a manner known to those skilled in the art and described e.g. in U.S. Pat. No. 5,149,425, the contents thereof with respect to filling, storage and use of such columns being incorporated by reference.

The conjugates Type II may be used as a single conjugate or as a mixture of different conjugates Type II as such or in the form of a composition adapted for affinity chromatography. Such mixture may comprise conjugates Type II differing with respect to polyamide backbone, macromolecular, macro- or microscopic entity and/or to antigenic group.

Preferred are compositions wherein the conjugate Type II comprises identical or different xenoantigenic groups or compositions comprising a mixture of conjugates Type II each conjugate comprising identical or different xenoantigenic groups, the xenoantigenic groups being derived from a disaccharide, preferably a group of formula IVb, from a trisaccharide, preferably a group of formula IVc or IVd, or from a pentasaccharide, preferably a group of formula IVe or IVf.

The method for removing the antibodies from the patient's body fluid may be performed according to known methods, e.g. as disclosed in U.S. Pat. No. 5,695,759. Preferred contact temperatures may be in the range of from 5° C. to 40° C., preferably of from 25° C. to 40° C. The body fluid may be directly reintroduced continuously or it may be collected and then be reintroduced. The method may be repeated as required prior to transplantation and/or after transplantation as long as removal of antibodies is of therapeutic benefit.

In accordance with the foregoing the present invention further provides:
(a) a conjugate Type II for use preferably as adsorbent in the affinity chromatography of body fluid;
(b) a method for removing antibodies from human body fluid, which method comprises extracorporally contacting said body fluid with a conjugate Type II as under (a) and reintroducing the body fluid into the patient's body;

(c) a composition comprising a conjugate Type II as under (a) or a mixture of such conjugates Type II as hereinbefore disclosed for use preferably in a method for removing xenoantibodies from human body fluid; and (d) an affinity chromatography cartridge comprising as adsorbent a conjugate Type II or a mixture therof or a composition as under (c).

Following examples illustrate the invention without limitation.

The following abbreviations are used in the examples: Ac: acetyl; Bn: benzyl; Bz: benzoyl; DBU: 1,8-diazabicyclo[5.4.0]undec-7-ene; DMF: N,N-dimethyl formamide; DMTST: dimethylmethylthio-sulfonium trifluoromethylsulfonate; eq: equivalent(s); GlcNAc: N-acetylglucosamine; n: degree of polymerization; Sepharose 4 fast flow: NHS-activated Sepharose 4 Fast Flow (Pharmacia Biotech); TESOTf: triethylsilyl trifluoromethane-sulfonate; UDP-Gal: uridine-O(6)diphosphoryl-α-D-galactose; RT: room temperature.

The mean molecular weights (M) and the polydispersities of the polylysine hydrobromides which are commercially obtainable from SIGMA are determined by means of viscosity measurements and SEC-LALLS (size exclusion chromatography/low angle laser light scattering) of the succinyl derivatives of the compounds.

A Preparation of Starting Compounds

EXAMPLE A1

Preparation of ethyl O-(2,3,4,6tetra-O-benzyl-α-D-galactopyranosyl)-(1→3)-O-(4-O-acetyl-2,6-di-O-benzoyl-1-thio-β-D-galactopyranoside) 3

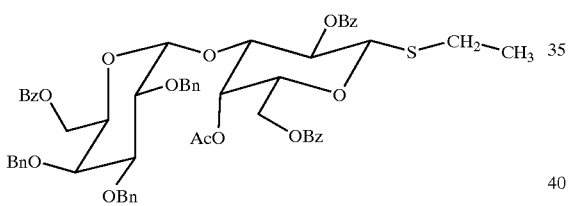

(3)

Ethyl 4-O-acetyl-2,6-di-O-benzoyl-1-thio-β-D-galactopyranoside 1 is prepared in analogy to the corresponding methylthio derivative [Garegg and Oscarson, Carbohyd. Res. 136:207–213 (1985)] and dissolved (2.12 g, 4.47 mmol) in dry diethyl ether (40 ml) and dry dichloromethane (25 ml). 1 ml of a solution of TESOTf (225 μl) in dry diethyl ether (10 ml) is added at −25° C. under argon. A solution of 2,3,4,6-tetra-O-benzyl-β-D-galactopyranosyl trichloroacetimidate 2 [7.50 g, 11.18 mmol; prepared according to Wegmann and Schmidt, J. Carb. Chem. 6:357–375 (1987)] in dry ether (22 ml) and dry dichloromethane (11 ml) is then added at −25° C. over 7 min. After stirring for 10 min at −25° C., NaHCO₃ (10%)(50 ml) is added and vigorous stirring is continued for 10 min. Water (100 ml) is added and the organic phase is separated. The aqueous phase is extracted twice with dichloromethane (80 ml each), the organic phases are washed with water (100 ml) and saturated brine (100 ml), dried with MgSO₄, and solvents are evaporated at reduced pressure. Chromatography of the crude product (10.25 g) on silica gel (700 g) with hexane/methyl acetate (5:1) as eluent gives ethyl O-(2,3,4,6-tetra-O-benzyl-α-D-galactopyranosyl)-(1→3)-O-(4-O-acetyl-2,6-di-O-benzoyl-1-thio-β-D-galactopyranoside) 3.

EXAMPLE A2

Preparation of (3-benzyloxycarbonylamino)-propyl 6-O-benzyl-2-deoxy-2-tetrachlorophthalimido-β-D-glucopyranoside 14

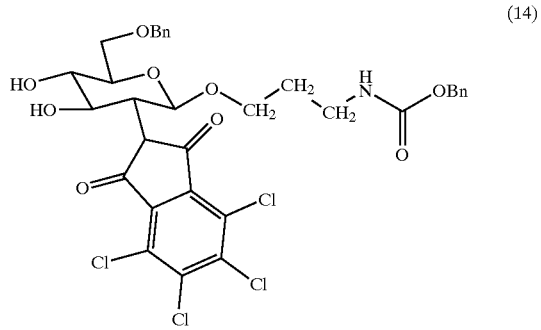

(14)

(a) 12.55 g (20.4 mmol) of 1,3,4,6-tetra-O-acetyl-2-deoxy-2-tetrachlorophthalimido-D-glucopyranose 9 prepared according to Castro-Palomino and Schmidt [Tetrahedron Lett. 36:5343–5346 (1995)] are treated with 4.1 M HBr in acetic acid (35 ml). After stirring for 18 h at RT, the mixture is carefully added to CHCl₃ (50 ml) and aqueous NaHCO₃ (10%) (400 ml) under ice-cooling and stirring. Neutralization (pH 7) with 10% NaHCO₃ is followed by extraction with CHCl₃ (3-times 150 ml). The organic phases are washed with saturated brine (200 ml), dried (Na₂SO₄), and solvent is evaporated under reduced pressure, affording crude 1-bromo-3,4,6-tri-O-acetyl-2-deoxy-2-tetrachlorophthalimido-D-glucopyranose 10, which is used for subsequent reactions without purification.

(b) 3-Benzyloxycarbonylamino-1-propanol (8.61 g, 41.3 mmol) and mercuric cyanide (10.45 g, 41.3 mmol) are added to a solution of crude 10 (13.15 g) in 165 ml of dry toluene. The suspension is stirred for 18 h, filtered through a cotton plug, and solvent is evaporated under reduced pressure. Chromatography of the residue on silica gel (1.3 kg) with hexane/ethyl acetate (2:1) as eluent gives (3-benzyloxycarbonylamino)-propyl 3,4,6-tri-O-acetyl-2-deoxy-2-tetrachlorophthalimido-β-D-glucopyranoside 11.

(c) 2.4 ml of a solution of sodium (820 mg) in dry methanol (40 ml) is added to a solution of acetate 11 (8.18 g, 10.7 mmol) in dry methanol (220 ml). The mixture is stirred at RT for 15 min and subsequently treated with Amberdite 15 H⁺ (2.8 g) for 15 min. Filtration and evaporation of solvent at reduced pressure gives (3-benzyloxycarbonylamino)-propyl 2-deoxy-2-tetrachlorophthalimido-β-D-glucopyranoside 12.

(d) p-Toluenesulfonic acid monohydrate (96 mg) is added to a solution of crude 12 (6.46 g) in acetonitril (60 ml) and α,α'-dimethoxy-toluene (2 ml). After stirring for 15 min at RT, the mixture is diluted with ethyl acetate (350 ml) and extracted with 10% aqueous NaHCO₃ (180 ml) followed by saturated brine (180 ml). The organic phase is dried with Na₂SO₄ and solvents are evaporated at reduced pressure. Chromatography of the residue (6.63 g) on silica gel (800 g), eluting with hexane/ethyl acetate (2:1), affords (3-benzyloxycarbonylamino)-propyl 4,6-di-O-benzylidene-2-deoxy-2-tetrachlorophthalimido-β-D-glucopyranoside 13.

(e) Mol sieves 4 Å (10 g) and NaCNBH₃ (2.91 g, 46.35 mmol) are added to a solution of acetal 13 (3.74 g, 5.15 mmol) in dry THF (150 ml) at 0° C. under argon. Under stirring etheral HCl is added until foaming cedes. Within 1.5 h two further portions of saturated etheral HCl (5 ml each) are added and stirring at 0° C. is continued for 18 h. Three additional 5 ml portions of etheral HCl are then added over 90 min before pouring the mixture to ice-water (250 ml) after 45 min. The flask is flushed with dichloromethane and the mixture is stirred for 10 min. Filtration (Celite) is followed by extraction CH₂Cl₂. The aqueous phase is extracted a second time with CH₂Cl₂ (100 ml) and the organic phases are washed with saturated brine (300 ml), dried with Na₂SO₄, and solvents are removed under reduced pressure. Chromatography of the residue (5.03 g) on silica gel (60 g) and elution with hexane/ethyl acetate (1:1) gives (3-benzyloxycarbonylamino)-propyl 6-O-benzyl-2-deoxy-2-tetrachlorophthalimido-β-D-glucopyranoside 14. ¹H-NMR (400 MHz, CDCl₃): 1.5–1.8 (m, CH₂); 3.0–3.25 (m, NCH₂, OH); 3.40 (b, OH); 3.5–3.6 and 3.77–3.87 (2m, OCH₂); 3.55–3.65 (m, H—C(4), —C(5)); 4.05–4.17 (m, H—C(2)); 4.2–4.3 (m, H—C(3)); 4.50 and 4.57 (2d, J=12, OCH₂C₆H₅); 4.9–5.05 (m, C(O)OCH₂C₆H₅); 5.1–5.2 (m, NH); 5.15 (d, J=8, H—C(1)); 7.2–7.4 (m, 2C₆H₅). The peak assignment is based on 2-dimensional ¹H/¹H-correlation (COSY) and ¹H/¹³C-correlation spectroscopy (HSQC).

EXAMPLE A3

Preparation of (3-acetamidoamino)-propyl O-(α-D-galactopyranosyl)-(1→3)-O-(β-D-galactopyranosyl)-(1→4)-O-(2-deoxy-2-acetamido-β-D-glucopyranoside) A5

EXAMPLE A4

Preparation of 3,4,6-tri-O-acetyl-2-deoxy-2-phthalimido-β-D-glucopyranosyl trichloroacetimidate (37)

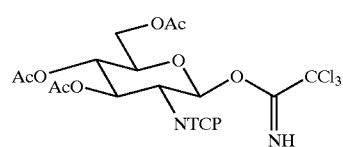

(37)

(a) To a solution of 10 according to example A2a (12.3 g, 18.73 mmol) in acetone (175 ml) water (55 ml) is added. After stirring for 18 h at RT solvent is evaporated and the residual aqueous solution is extracted with toluene (3×100 ml). Chromatography of the residue of the organic phases (silica gel 500 g, CH₂Cl₂ & 2% CH₃OH) gives 3,4,6-tri-O-acetyl-2-deoxy-2-phthalimido-D-glucopyranose (36) (mostly β-anomer).

(b) To a solution of 36 (4.0 g, 6.98 mmol) and trichloroacetonitril (4.2 ml, 14.88 mmol) in CH₂Cl₂ (25 ml) 18 g of finely powdered dry K₂CO₃ are added. After stirring for 60 min at RT the mixture is filtered through Celite®. Chromatography (silica gel, 500 g, hexane/ethyl acetate= 2:1) gives 37 (β-anomer).

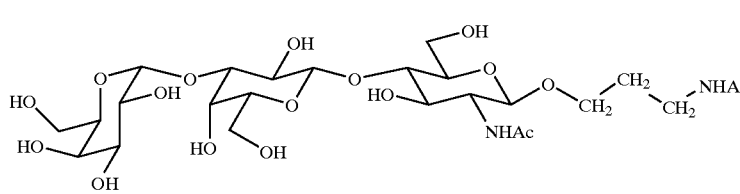

(A5)

A solution of 8 (13 mg, 0.0216 mmol), prepared according to example A9e, N-acetoxysuccinimide (3.4 mg, 0.0324 mmol), and diisopropyl-ethyl-amine (7.3 µl, 0.0432 mmol) in DMF (1 ml) is stirred for 15 h at RT. Evaporation of solvents at reduced pressure and chromatography (5 g of silica gel, chloroform/methanol/water=30:30:2) affords A5; ¹H-NMR (400 MHz, D₂O), selected signals: 1.6–1.75 (m, OCH₂CH₂CH₂NH); 2.90 and 2.95 (2s, 2 NH—COCH₃); 3.02–3.12 and 3.12–3.22 (2m, O(CH₂)₂CH₂NH); 4.43 and 4.47 (2d, J=8, H—C(1), H—C(1')); 5.08 (d, J=4, H—C(1")).

EXAMPLE A5
Preparation of (3-benzyloxycarbonylamino)-propyl O-(2,6-di-O-benzoyl-β-D-galactopyranosyl)-(1→4)-O-(2,3,6-tri-O-benzoyl-β-D-glucopyranoside) 35

(35)

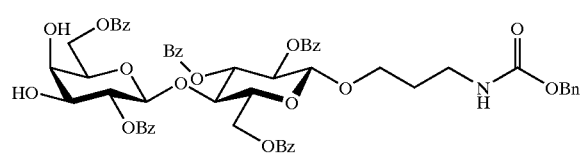

(a) To a suspension of dried lactose 28 (100 g, 0.28 mol) in pyridine (500 ml) benzoyl chloride (520 ml, 5.0 mol) is added dropwise at 0° C. and under mechanical stirring. After addition of 4-(N,N-dimethylamino)-pyridine the mixture is stirred at RT for 3 days and at 100° C. for additional 2 days. The reaction mixture is then poured to ice-water and extracted with ethyl acetate. The organic phase is washed with saturated NaHCO₃-solution and brine. Drying with Na₂SO₄, evaporation of solvents, and coevaporation of pyridine with toluene affords crude O-(2,3,4,6-tetra-O-benzoyl-β-D-galactopyranosyl)-(1→4)-O-(1,2,3,6-tetra-O-benzoyl-D-glucopyranose) (29) as anomeric mixture.

(b) 29 (150 g, 0.127 mol) is dissolved in dichloromethane (500 ml) and 4.1 M HBr in acetic acid (100 ml) is added at −10° C. The mixture is slowly warmed to RT and the conversion is monitored by TLC (petrol ether/ethyl acetate=3:1). After completion the mixture is carefully neutralised with 4 N NaOH and then poured to ice-water. Extraction with ethyl acetate, washing of the extracts with saturated NaHCO₃-solution, brine, and water, evaporation of solvents, and drying of the residue at high vacuum gives O-(2,3,4,6-tetra-O-benzoyl-βD-galactopyranosyl)-(1→4)-O-(1-deoxy-1-bromo-2,3,6-tri-O-benzoyl-α-D-glucopyranose) (30).

(c) 30 (18.9 g, 16.7 mmol) and N-benzyloxycarbonyl propanolamine (7.0 g, 33.5 mmol) are dissolved in toluene (abs., 150 ml) under Ar. With stirring Hg(CN)₂ (8.45 g, 33.45 mmol) and Hg Br₂ (1.21 g, 3.35 mmol) are added. The mixture is stirred at RT for 18 h, then filtered over Celite® and the residue is purified by flash chromatography (eluent toluene/n-hexene/ethyl acetate 5:5:2, v/v) to yield (3-benzyloxycarbonylamino)-propyl O-(2,3,4,6-tetra-O-benzoyl-β-D-galactopyranosyl)-(1→4)-O-(2,3,6-tri-O-benzoyl-β-D-glucopyranoside) (31).

(d) 31 (16.3 g, 12.9 mmol) is dissolved under Ar at RT in methanol (abs., 90 ml). A freshly prepared solution of NaOMe in methanol (1 N, 3.9 ml) is added and the solution is stirred for 16 h. Then additional NaOMe solution (3.9 ml) is added and stirring continued for another 7 h. The mixture is neutralized with acetic acid and evaporated. The residue is purified by flash chromatography (eluent CH₂Cl₂/MeOH 2:1, v/v) to give (3-benzyloxycarbonylamino)-propyl O-(β-D-galactopyranosyl)-(1→4)-O-(β-D-glucopyranoside) 32.

(e) To a solution of 32 (6.5 g, 12.18 mmol) in acetone (500 ml) p-toluenesulfonic acid (770 mg, 4.06 mmol) is added at reflux temperature. After 20 min the reaction mixture is quenched with NaHCO₃-solution (10%) and the solvent is evaporated. The residue is extracted several times with dichloromethane, washed with water, dried and evaporated. The crude product is purified by flash chromatography (eluent ethyl acetate/methanol 9:1, v/v) to give (3-benzyloxycarbonylamino)-propyl O-(3,4-di-O-isopropylidene-β-D-galactopyranosyl)-(1→4)-O-(β-D-glucopyranoside) 33.

(f) To a solution of 33 (2.2 g, 3.84 mmol) in pyridine (abs., 60 ml) benzoylchloride (6.68 ml, 57.6 mmol) is added dropwise with stirring at RT under argon. The solution is stirred for 16 h. The mixture is evaporated and redissolved in dichloromethane. The organic phase is washed several times with 1N HCl, water and neutralized with NaHCO₃-solution (10%).

After drying solvent is evaporated, and the residue purified by flash chromatography (eluent toluene/acetone 15:1, v/v) to give (3-benzyloxycarbonylamino)-propyl O(2,6-di-O-benzoyl-3,4-di-O-isopropylidene-β-D-galactopyranosyl)-(1→4)-O-(2,3,6-tri-O-benzoyl-β-D-glucopyranoside) (34).

(g) A suspension of 34 (3.4 g, 3.11 mmol) in acetic acid/water (60 ml, 4:1, v/v) is heated under argon at 100° C. for 40 min. The mixture is cooled to RT and evaporated. The residue is coevaporated several times with toluene, and purified by flash chromatography (eluent toluene/acetone 5:1, v/v) to give (3-benzyloxycarbonylamino)-propyl O-(2,6-di-O-benzoyl-β-D-galactopyranosyl)-(1→4)-O-(2,3,6-tri-O-benzoyl-β-D-glucopyranoside) (35).

EXAMPLE A6

Preparation of (3-benzyloxycarbonylamino)-propyl O-(α-D-galactopyranosyl)(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(β-D-glucopyranoside) (A9)

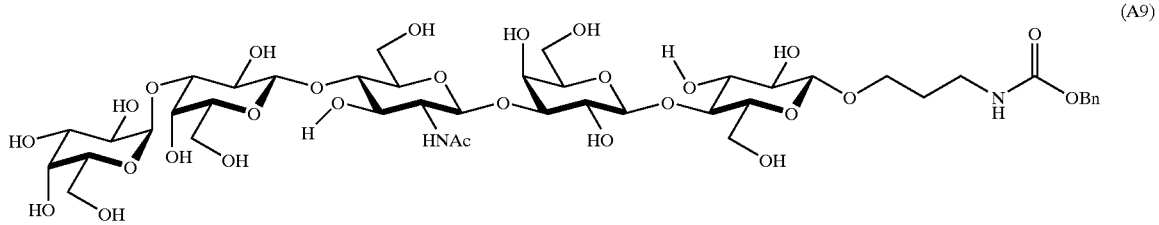

(A9)

(i) (a) A solution of 37 (dry, 3.5 g, 4.88 mmol) and 35 (dry, 2.7 g, 2.56 mmol) in dichloromethane (abs., 30 ml) is cooled to −20° C. and TESOTf (58 μl, 0.1 eq.) is added. After 3 h additional TESOTf (0.2 eq.) is added. After another h the reaction mixture is neutralized with triethylamine, evaporated and coevaporated twice with toluene. The residue is purified by flash chromatography (eluent toluene/acetone 7:1, v/v) to give (3-benzyloxycarbonylamino)-propyl O(2-deoxy-2-tetrachlorophthalimido-3,4,6-tri-O-acetyl-β-D-glucopyranosyl)-(1→3)-O-(2,6-di-O-benzoyl-β-D-galactopyranosyl)-(1→4)-O-(2,3,6-tri-O-benzoyl-β-D-glucopyranoside) 38.

(b) A solution of 38 (2.64 g, 1.64 mmol) in ethanol (abs., 80 ml) is treated at 60° C. with ethylenediamine (220 μl, 3.28 mmol) under argon. After 2 h additional ethylenediamine (110 μl ) is added and after another h the mixture is evaporated and coevaporated several times with toluene. The residue is treated with pyridine/acetic anhydride (120 ml, 2:1, v/v) and stirred at RT under argon for 60 h. The mixture is evaporated and coevaporated several times with toluene and the residue is purified by flash chromatography (toluene/acetone 3:1, v/v) to give (3-benzyloxycarbonylamino)-propyl O-(2-deoxy-2-acetamido-3,4,6-tri-O-acetyl-β-D-glucopyranosyl)-(1→3)-O-(4-O-acetyl-2,6-di-O-benzoyl-β-D-galactopyranosyl)-(1→4)-O-(2,3,6-tri-O-benzoyl-β-D-glucopyranoside) 39.

(c) A solution of 39 in methanol (abs., 100 ml) is treated with a solution of freshly prepared NaOMe (1N, 1 ml) and stirred at RT under argon for 16 h. The mixture is neutralized with TFA and evaporated. The residue is purified by flash chromatgraphy (dichloromethane/methanol 2:1, v/v) to give (3-benzyloxycarbonylamino)-propyl O-(2-deoxy-2-acetamido-β-D-glucopyranosyl)-(1→3)-O-(β-D-galactopyranosyl)-(1→4)-O-(β-D-glucopyranoside) 40.

(d) To a clear solution of 40 (230 mg, 0.312 mmol), UDP-Gal (273 mg, 0.447 mmol), BSA (17 mg) and MnCl$_2$.6 H$_2$O (73.5 mg, 0.313 mmol) in 20 ml of sodium cacodylate buffer (0.1 M, pH 7.3) β-(1→4)-galactosyl-transferase (2.5 U, 500 µl of Sigma No G-5507, 25 U/5 ml) and alkaline phosphatase (25 µl, Boehringer No. 108146, 7500 U/498 µl) are added and the mixture is incubated at 37° C. overnight. The mixture is then passed over a RP-18 column (2.5 cm Ø, 10 cm length), washed with water and eluted with methanol to give (3-benzyloxycarbonylamino)-propyl O-(β-D-galactopyranosyl)-(1→4)-O-(2-deoxy-2-acetamido-β-D-glucopyranosyl)-(1→3)-O-(β-D-galactopyranosyl)-(1→4)-O-(β-D-glucopyranoside) 41.

(e) To a solution of MnCl$_2$.6 H$_2$O (317.2 mg, 1.6 mmol) in H$_2$O (19 ml) and 0.5 M sodium cacodylate buffer (6.8 ml, pH 6.5) 225 mg (0.250 mmol) of 41, UDP-Gal (219 mg, 0.36 mmol) and BSA (20 mg) are added. This mixture is incubated at 37° C. with 2.5 ml of recombinant α-(1→3)-galactosyl-transferase [3 U/ml, prepared according to Joziasse et al., Europ. J. Biochem. 191:75 (1990)] and 25 µl of calf intestine alkaline phosphatase (Boehringer No 108146, 7500 U/498 µl) for 48 h. The mixture is passed over a short C-18 reversed phase column (2.5 cm Ø, 10 cm length), washed with water and eluted with methanol. Chromatography of the residue over silica gel (CH$_2$Cl$_2$/CH$_3$OH/H$_2$O=10:2; 0.2) gives A9.

(ii) (a) O-(α-D-galactopyranosyl)-(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(β-D-glucopyranose) (23) (Chem. Abstr. Reg. No. 177331-58-7, 500 mg, 0.54 mmol) is dissolved in pyridine (10 ml) and acetic anhydride (5 ml) is slowly added. The solution is stirred at RT overnight. The clear solution is evaporated and codistilled several times with toluene. The residue is dissolved and purified by flash 40 system on silica gel (eluent toluene/acetone 3:2 v/v) to give after concentration O-(2,3,4,6-tetra-O-acetyl-α-D-galactopyranosyl)-(1→3)-O-(2,4,6-tri-O-acetyl-β-D-galactopyranosyl)-(1→4)-O-(2-deoxy-2-acetamido-3,6-di-O-acetyl-β-D-glucopyranosyl)-(1→3)-O-(2,4,6-tri-O-acetyl-β-D-galactopyranosyl)-(1→4)-O-(1,2,3,6-tetra-O-acetyl-β-D-glucopyranose) (24) as colourless syrup.

(b) 24 (770 mg, 0.499 mmol) is dissolved in DMF (abs, 50 ml) under argon. Molecular sieves (4 A, 1 g) are added and the mixture is stirred at RT for 30 min. Then dry hydrazinium acetate (140 mg, 1.50 mmol) is added to the mixture and stirred for 3 h at 50° C. The reaction mixture is filtered through a small pad of Celite® and ice water is added. The product is extracted with ethyl acetate, washed, dried (MgSO$_4$) and the solution is evaporated to dryness. The residue is purified by chromatography on silica gel to give O-(2,3,4,6-tetra-O-acetyl-α-D-galactopyranosyl)-(1→3)-O-(2,4,6-tri-O-acetyl-β-D-galactopyranosyl)-(1→4)-O-(2-deoxy-2-acetamido-3,6-di-O-acetyl-β-D-glucopyranosyl)-(1→3)-O-(2,4,6-tri-O-acetyl-β-D-galactopyranosyl)-(1→4)-O-2,3,6-tri-O-acetyl-β-D-glucopyranose) (25).

(c) 25 (dried, 570 mg, 0.38 mmol) is dissolved in dichloromethane (abs., 3 ml) under argon. Trichloroacetonitrile (600 µl) is added, followed by dropwise addition of DBU until the reaction mixture turns to yellow (3–4 drops). The mixture is stirred at RT until TLC (toluene/acetone, 1:1, v/v) shows complete conversion of the starting material to a higher moving product (R$_f$ 0.48). The solution is carefully evaporated to dryness and directly purified by flash chromatography (eluent toluene/acetone, 1:1, v/v) to yield O-(2,3,4,6-tetra-O-acetyl-α-D-galactopyranosyl)-(1→3)-O-(2,4,6-tri-O-acetyl-β-D-galactopyranosyl)-(1→4)-O-(2-deoxy-2-acetamido-3,6-di-O-acetyl-β-D-glucopyranosyl)-(1→3)-O-(2,4,6-tri-O-acetyl-β-D-galactopyranosyl)-(1→4)-O-(2,3,6-tri-O-acetyl-α-D-glucopyranosyl) trichloroacetimidate (26) as a colourless sirup.

(d) 26 (40 mg, 24.3 µmol) and N-carbobenzyloxy-1-propanolamine (15.5 mg, 73.0 µmol) are dissolved under argon in dichloromethane (abs., 1 ml) and n-hexane (abs., 3 ml), about 1 g of grinded MS (4A) is then added, and the mixture is stirred at RT for 30 min before TESOTf (5 µl) is added. After 30 min the mixture is neutralized with triethylamine and evaporated to dryness. The residue is purified by flash chromatography (eluent toluene/acetone 3:2, v/v) and (3-benzyloxycarbonylamino)-propyl O-(2,3,4,6-tetra-O-acetyl-α-D-galactopyranosyl)-(1→3)-O-(2,4,6-tri-O-acetyl-β-D-galactopyranosyl)-(1→4)-O-(2-deoxy-2-acetamido-3,6-di-O-acetyl-β-D-glucopyranosyl)-(1→3)-O-(2,4,6-tri-O-acetyl-β-D-galactopyranosyl)-(1→4)-O-(2,3,6-tri-O-acetyl-β-D-glucopyranoside) 27 is isolated.

(e) 27 (59 mg, 34.5 µmol) is suspended in methanol (abs., 1 ml). A solution of freshly prepared sodium methylate in methanol (1N, 100 µl) is added and the mixture is stirred over-night at RT under argon. Finally water (0.5 ml) is added and stirring continued. After 1 h the solution is neutralized with TFA (10 µl) and evaporated to dryness. Purification of the residue by flash chromatography gives A9. [α]$_D$+44.4 (c 1.075, H$_2$O). MS (ESI+) 1083 (M+Na$^+$). $^1$H-NMR (500 MHz, CDCl$_3$), selected signals: 4.31 (d, J=8, H—C(1) β-glucose and β-galactose); 4.44 (d, J=8, H—C(1) β-galactose); 4.59 (d, J=8, H—C(1) N-Acetyl-62-glucosamine); 5.30 (d, J=4, H—C(1) α-galactose).

EXAMPLE A7

Preparation of [3-(4-mercapto-butyroyl)amino]-propyl 2-desoxy-2-acetamido-β-D-glucopyranoside A6

(A6)

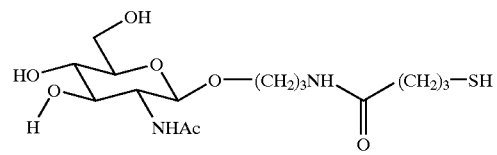

To a solution of 3-amino-propyl 2-deoxy-2-acetamido-β-D-glucopyranoside 18a (500 mg, 1.80 mmol) and γ-thiobutyrolactone (1.84 g, 18 mmol) in 15 ml of dry and oxygen-free methanol triethylamine (1.82 g, 18 mmol) is added. The solution is boiled for 16 h under reflux (argon). Solvent is evaporated under reduced pressure and the residue is chromatographed on silica gel. Elution with ethyl acetate/methanol (3:1) affords A6. $^1$H-NMR (400 MHz, CD$_3$OD): 1.72 (m, OCH$_2$CH$_2$CH$_2$NH); 1.88 (quint, J=7, NH—CO—CH$_2$CH$_2$CH$_2$SH); 1.99 (s, COCH$_3$); 2.33 (t, J=7, NH—CO—CH$_2$(CH$_2$)$_2$SH); 2.51 (t, J=7, NH—CO—(CH$_2$)$_2$CH$_2$SH); 3.15–3.95 (m, 10H); 4.36 (d, J=8.5, H—C(1)).

EXAMPLE A8

Preparation of [6-(4-mercaptobutyroyl)amino]hexyl-O-(α-galactopyranosyl)-(1→3)-O-(β-galactopyranoside) (A4)

(a) To a solution of 3 according to example A1 (1.0 g, 1.004 mmol) and (6-benzyloxycarbonylamino)-1-hexanol (0.504 g, 2.008 mmol) in 4 ml of dry dichloromethane powdered molecular sieves (2.0 g, 4 Å) are added under argon and the suspension is stirred for 20 min at RT. 1 ml portions of a solution of DMTST (0.778 g, 3.012 mmol) in dichloromethane (9 ml) containing molecular sieves (2.5 g, 4 Å) are added in 10 min intervals, while stirring at RT and under argon is continued. After the addition of 7 portions the mixture is poured to ethyl acetate, 10% aqueous NaHCO$_3$, and crushed ice. The mixture is stirred for 10 min and filtered through Celite™. The aqueous phase is separated and extracted twice with ethyl acetate. The organic phases are washed with 10% aqueous NaCl and saturated brine, dried with Na$_2$SO$_4$, and volatiles are evaporated at reduced pressure. Chromatography (150 g of silica gel) of the residue (1.6 g) eluting with toluene/ethyl acetate (10:1) affords (6-benzyloxycarbonylamino)-hexyl O-(2,3,4,6-tetra-O-benzyl-α-D-galactopyranosyl)-(1→3)-O-(4-O-acetyl-2,6-di-O-benzoyl-β-D-galactopyranoside) 15.

(b) To a solution of 15 (925 mg, 0.781 mmol) in methanol (30 ml) and water (3 ml) LiOH.H$_2$O (328 mg, 7.81 mmol) is added. The mixture is heated to 60° C. under argon for 6 h. Solvents are evaporated at reduced pressure and the residue is partitioned between CHCl$_3$ and water. The CHCl$_3$ layer is separated and washed with water, the aqueous phases are extracted with CHCl$_3$. The organic phases are dried with Na$_2$SO$_4$ and evaporated. Chromatography (100 g of silica gel) with toluene/ethyl acetate (1:1) as eluent gives (6-benzyloxy-carbonylamino)-hexyl O-(2,3,4,6-tetra-O-benzyl-α-D-galactopyranosyl)-(1→3)-O-(β-D-galactopyranoside) 16.

(c) To a solution of 16 (479 mg, 0.512 mmol) in dioxane (16 ml) and water (9 ml) Pd(OH)$_2$ (20% on charcoal, 350 mg) is added under argon. The suspension is stirred for 36 h under H$_2$. The mixture is filtered through Celite™ and the filtrate is evaporated under reduced pressure. The residue is redissolved in dioxane (16 ml) and water (9 ml). After the addition of Pd(OH)$_2$ (20% on charcoal, 350 mg) the suspension is stirred for 18 h under H$_2$. Filtration (Celite™) and evaporation of solvents is followed by filtration through an Acrodisc™ in water. Lyophilisation of the filtrate gives 6-amino-hexyl O-(α-D-galactopyranosyl)-(1→3)-O-(β-D-galactopyranoside) 17.

(A4)
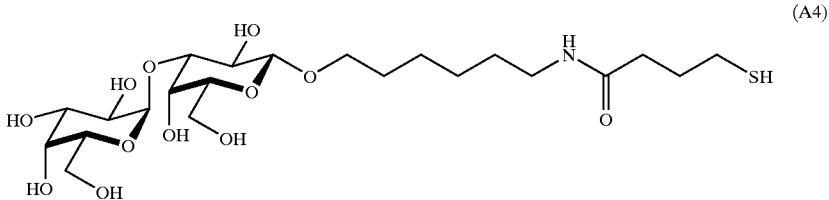

(d) A solution of compound 17 (100 mg, 0.227 mmol), γ-thiobutyrolactone (196 μl, 2.27 mmol), and triethylamine (316 μl, 2.27 mmol) in dry, oxygen-free DMF (7 ml) is heated for 24 h to 90° C. under argon. Evaporation of volatiles under reduced pressure at 40° C. and chromatography (10.5 g silica gel) of the residue (160 mg) with chloroform/methanol/water (30:30:5) as eluent affords A4. $^1$H-NMR (400 MHz, D$_2$O), selected signals: 1.15–1.35 (m, O(CH$_2$)$_2$(CH$_2$)$_2$(CH$_2$)$_2$NH); 1.35–1.45 (m, O(CH$_2$)$_4$CH$_2$CH$_2$NH); 1.45–1.6 (m, OCH$_2$CH$_2$(CH$_2$)$_4$NH); 1.77 (quint, J=7.5, NH—CO—CH$_2$CH$_2$CH$_2$SH); 2.24 (t, J=7.5, NH—CO—CH$_2$(CH$_2$)$_2$SH); 2.43 (t, J=7.5, NH—CO—(CH$_2$)$_2$CH$_2$SH); 3.07 (t, J=7, O(CH$_2$)$_5$CH$_2$NH); 4.34 (d, J=8, H—C(1)); 5.04 (d, J=4, H—C(1')).

EXAMPLE A9

Preparation of [3-(4-mercaptobutyroyl)amino]propyl O-(α-D-galactopyranosyl)-(1→3)-O-(β-D-galactopyranosyl)-(1→4)-O-(-2-deoxy-2-acetamido-β-D-glucopyranoside) (A2)

(A2)
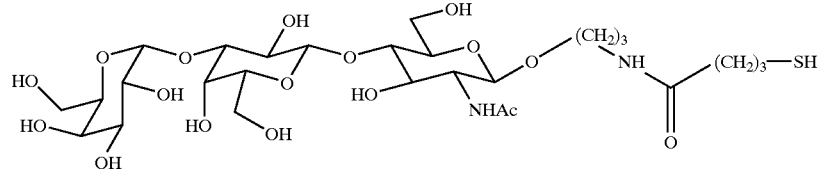

(a) Freshly activated powdered mol sieves 4 Å (2.0 g) are added to a solution of 3 (2.3 g, 2.31 mmol) and 14 (1.12 g, 1.54 mmol) in dry dichloromethane (10 ml). After stirring this suspension for 30 min under argon, a solution of DMTST (0.99 g, 3.85 mmol) in CH$_2$Cl$_2$ (7.5 ml) containing powdered mol sieves 4 Å (1.5 g) is added in 5 portions with 20 min intervals. Addition of aqueous NaHCO$_3$ (10%)(20 ml) is followed by stirring for 10 min and addition of water (50 ml) and ethyl acetate (150 ml). After filtration over Celite™ and washing with ethyl acetate the aqueous phase is separated and extracted twice with ethyl acetate. The organic phase is washed with saturated brine, dried with Na$_2$SO$_4$, and solvents are evaporated at reduced pressure. Chromatography of the crude product (3.43 g) on silica gel (550 g) and elution with hexane/methyl acetate (3:1) gives (3-benzyloxycarbonylamino)-propyl O-(2,3,4,6-tetra-O-benzyl-α-D-galactopyranosyl)-(1→3)-O-(4-O-acetyl-2,6-di-O-benzoyl-β-D-galactopyranosyl)-(1→4)-O-(6-O-benzyl-2-deoxy-2-tetrachlorophthalimido-β-D-glucopyranoside) 4.

(b) A mixture of 4 (1.412 g, 0.850 mmol), 1,2-diaminoethane (86 μl), and ethanol (40 ml) is heated under argon to 60° C. After 140 min additional 1,2-diaminoethane (36 μl) is added and heating is continued for 1 h. Solvent is then evaporated under reduced pressure and the residue is chromatographed on silica gel (170 g). Elution with CH$_2$Cl$_2$/2-propanol (15:1) affords (3-benzyloxycarbonylamino)-propyl O-(2,3,4,6-tetra-O-benzyl-α-D-galactopyranosyl)-(1→3)-O-(4-O-acetyl-2,6-di-O-benzoyl-β-D-galactopyranosyl)-(1→4)-O-(6-O-benzyl-2-deoxy-3-amino-β-D-glucopyranoside) 5.

(c) Acetic anhydride (15 ml) is added to a solution of amine 5 (975 mg, 0.699 mmol) in pyridine (15 ml). After stirring for 18 h at RT, solvent and reagent are evaporated at 40° C. under reduced pressure. Chromatography of the residue (1.26 g) on silica gel (125 g) with dichloromethane/2-propanol (15:1) as eluent gives (benzyloxycarbonylamino)-propyl O-(2,3,4,6-tetra-O-benzyl-α-D-galactopyranosyl)-(1→3)-O-(4-O-acetyl-2,6-di-O-benzoyl-β-D-galactapyranosyl)-(1→4)-O-(3-O-acetyl-6-O-benzyl-2-deoxy-2-acetamino-β-D-glucopyranoside) 6.

(d) Lithium hydroxide monohydrate (255 mg, 6.08 mmol) is added to a solution of 6 (898 mg, 0.608 mmol) in methanol (25 ml) and water (2.5 ml). After stirring for 3 h 15 min at 60° C., solvents are evaporated under reduced pressure from the thick suspension. The residue is dissolved in ethyl acetate (150 ml) and the solution is washed with water (3-times 70 ml) and saturated brine (50 ml). The aqueous washings are extracted with ethyl acetate once. The organic phases are dried with Na$_2$SO$_4$, and solvent is evaporated. Chromatography of the residue (732 mg) on silica gel (120 g) with dichloromethane/2-propanol (10:1) as eluent, followed by ethyl acetate/acetone/2-propanol (5:1:1) affords (3-benzyloxycarbonylamino)-propyl O-(2,3,4,6-tetra-O-benzyl-α-D-galactopyranosyl)-(1→3)-O-(β-D-galactopyranosyl)-(1→4)-O-(6-O-benzyl-2-deoxy-2-acetamido-β-D-glucopyranoside) 7.

(e) Perlmann-catalyst (1.46 g 20% Pd(OH)$_2$ on charcoal) is added to a solution of 7 (610 mg, 0.514 mmol) in dioxane (50 ml) and water (28 ml). The suspension is vigorously stirred under H$_2$ for 22 h. After filtration (Celite) the filtrate is evaporated and the residue redissolved in dioxane (50 ml) and water (28 ml). Fresh catalyst (1.46 g 20% Pd(OH)$_2$ on charcoal) is added and stirring under H$_2$ is continued for 3 days. Filtration and evaporation of solvents at reduced pressure gives 290 mg (93%) of crude (3-amino)-propyl O-(α-D-galactopyranosyl)-(1→3)-O-(β-D-galactopyranosyl)-(1→4)-O-(2-deoxy-2-acetamido-β-D-glucopyranoside) 8.

(f) 100 mg (0.166 mmol) of compound 8 are dissolved in 5 ml of dry, oxygen-tree DMF. After addition of γ-thiobutyrolactone (0.144 ml, 1.66 mmol) and triethylamine (0.231 ml, 1.66 mmol) the mixture is heated to 90° C. for 18 h under argon. Solvent and volatiles are removed by evaporation under vacuum at 45° C. Chromatography (15 g of silica gel) of the residue (140 mg) with chloroform/methanol/water (30:30:10) affords A2. $^1$H-NMR (400 MHz, D$_2$O), selected signals: 1.68 (quint., J=6.0, OCH$_2$CH$_2$CH$_2$NH); 1.78 (quint., J=7.5, NH—CO—CH$_2$CH$_2$CH$_2$SH), 1.95 (s, COCH$_3$); 2.25 (t, J=7.5, NH—CO—CH$_2$CH$_2$CH$_2$SH); 2.44 (t, J=7.5, NH—CO—CH$_2$CH$_2$CH$_2$SH); 3.03–3.13 and 3.13–3.23 (2m, OCH$_2$CH$_2$CH$_2$NH); 4.43 and 4.46 (2d, J=8, H—C (1), H—C(1')); 5.03 (d, J=4, H—C(1")). MS/EI: 703 (M-H)$^-$.

EXAMPLE A10

Preparation of [3-(4-mercapto-butyroyl)amino] propyl O-(α-D-galactopyranosyl)(1→3)-O-(β-D-galactopyranosyl(1→4)-O-(β-D-glucopyranoside) (A3)

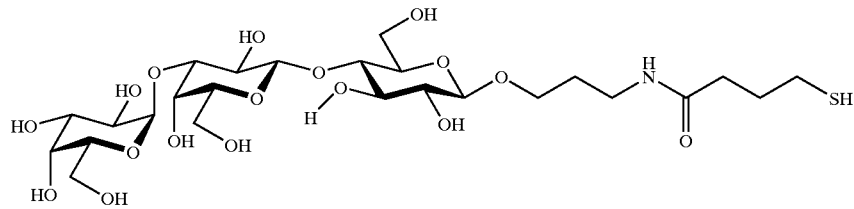

(A3)

A solution of 3-aminopropyl O-(α-D-galactopyranosyl)-(1→3)-O-(β-D-galactopyranosyl)-(1→4)-O-(β-D-glucopyranoside) 18 (74 mg, 0.1319 mmol), prepared synthetically from lactose and galactose according to standard methods, γ-thiobutyrolactone (114 μl, 1.319 mmol), and triethylamine (184 μl, 1.319 mmol) in dry, oxygen-free methanol (10 ml) is heated under reflux for 18 h (argon). After separation of some insoluble material (9 mg) by filtration and evaporation of the filtrate at reduced pressure, the residue (119 mg) is chromatographed on silica gel (15 g). Elution with chloroform/methanol/water (30:30:10) gives A3. $^1$H-NMR (400 MHz, D$_2$O), selected signals: 1.65–1.85 (m, OCH$_2$CH$_2$CH$_2$NH, NH—CO—CH$_2$CH$_2$SH); 2.25 (t, J=7.5, NH—CO—CH$_2$(CH$_2$)$_2$SH); 2.45 (t, J=7.5, NH—CO—(CH$_2$)$_2$CH$_2$SH); 3.1–3.25 (m, H—C(2), O(CH$_2$)$_2$ CH$_2$NH); 4.38 and 4.42 (2d, J=8, H—C(1), H—C (1')); 5.04 (d, J=4, H—C(1")).

EXAMPLE A11

Preparation of [N-(4-mercaptobutyroyl)]-glycinoyl N-(α-D-galactopyranosyl)-(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(1-deoxy-1-amino-β-D-glucopyranoside) (A8)

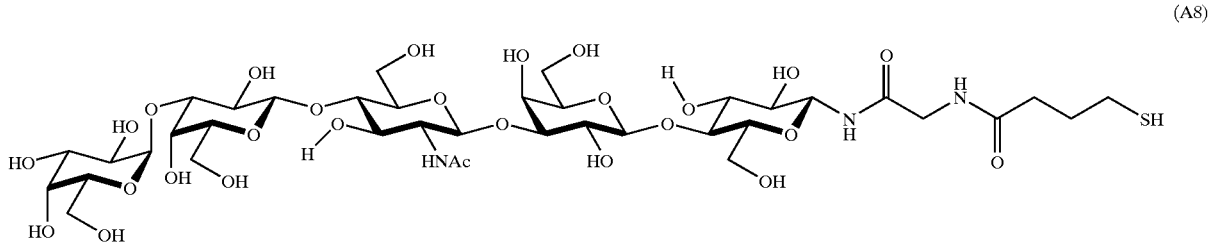

(A8)

A degassed solution/suspension of glycinoyl N-(α-D-galactopyranosyl)-(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(1-deoxy-1-amino-β-D-glucopyranoside) (commercially available)(22, 205 mg, 0.222 mmol), 1-thiobutyrolactone (192 μl, 2.22 mmol), triethylamine (310 μl, 2.22 mmol), and dithio-D/L-threitol (51.4 mg, 0.333 mmol) in dry DMF (10 ml) is heated for 3.5 h to 90° C. under argon. Volatiles are evaporated under reduced pressure (high vacuum) and the residue is chromatographed on silica gel (25 g). Elution with chloroform/methanol/water (30:30:10) and lyophilisation affords A8. $^1$H-NMR (400 MHz, D$_2$O), selected signals: 1.8 (quint., J=7, CO—CH$_2$CH$_2$CH$_2$SH); 1.93 (s, NH—COCH$_3$); 2.34 (t, J=7, CO—CH$_2$CH$_2$CH$_2$SH); 2.47 (t, J=7, CO—CH$_2$CH$_2$CH$_2$SH); 3.32–3.4 (m, H—C(2), glucose); 3.87 (m, CO—CH$_2$—NH); 4.33 and 4.44 (2d, J=8, 2 H—C(1), β-galactose); 4.60 (d, J=8, H—C(1) N-acetylglucosamine); 4.91 (d, J=9, H—C(1), glucose); 5.04 (d, J=4, H—C(1) α-galactose).

EXAMPLE A12

Preparation of [3-(4-mercapto-butyroyl)amino]-propyl O-(α-D-galactopyranosyl)-(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(β-D-glucopyranoside) (A10)

(a) A9 (25 mg, 23.6 μmol) is dissolved in water (5 ml) and palladium hydroxide (5 mg) is added. The mixture is stirred overnight under hydrogen at RT. The catalyst is removed by filtering the mixture through a small pad of Celite®. After evaporation and lyophilisation from water 3-amino-propyl O-(α-D-galactopyranosyl)-(1→3)-O-(β-D-galactopyranosyl)-(1→4)-O-(2-deoxy-2-acetamido-β-D-glucopyranosyl)-(1→3)-O-(β-D-galactopyranosyl)-(1→4)-O-(β-D-glucopyranoside) 42 is obtained as a colourless powder.

(b) To a solution of 42 (450 mg, 0.4855 mmol) and dithio-threitol (112 mg, 0.728 mmol) in dry DMF (30 ml) 420 μl of γ-thiobutyrolactone and 680 μl of triethylamine are added. After degassing the solution is heated for 18 h to 90° C. under argon. Evaporation of solvent at 50° C. under reduced pressure and chromatography on silica gel (50 g, chloroform/methanol/water=30:30:10) affords A10. $^1$H-NMR (400 MHz, D$_2$O), selected signals: 1.65–1.85 (m, OCH$_2$CH$_2$CH$_2$NHCOCH$_2$CH$_2$CH$_2$SH); 2.25 (t, J=7, COCH$_2$(CH$_2$)$_2$SH); 2.43 (t, J=7, CO(CH$_2$)$_2$CH$_2$SH); 3.10–3.27 (m, O(CH$_2$)$_2$CH$_2$NH, H—C(2) β-glucose); 4.33 and 4.44 (2d, J=8, 2 H—C(1) β-galactose); 4.36 (d, J=8, H—C(1) β-glucose); 4.6 (d, J=8, H—C(1) 2-deoxy-2-acetamido-β-D-glucose); 5.03 (d, J=4, H—C(1) α-galactose).

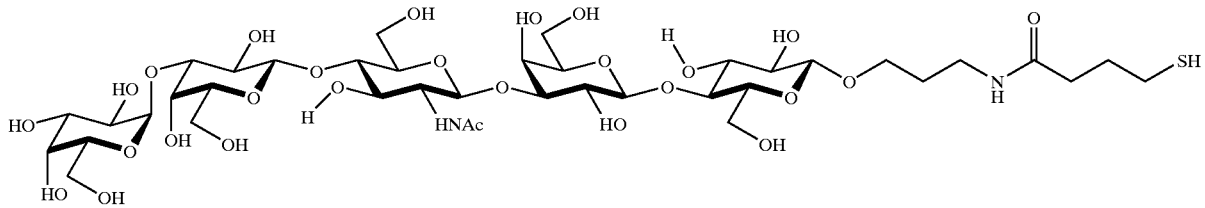

(A10)

EXAMPLE A13

Preparation of N-{8-[N-diphenyl-(4-methoxyphenyl)-methyl]-amino-3,6-dioxa-1-octyl}-4-mercapto-butyramide A7

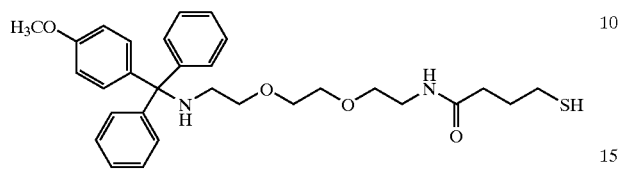

(A7)

(a) To a stirred emulsion of triethylene glycol (39 g, 0.26 mol) in ether (200 ml) and triethylamine (50 ml) cooled to 0° C. methanesulfonyl chloride (10.1 ml, 0.13 mol) is added during 3 h. The mixture is allowed to reach RT and stirring is continued for 20 min. Solvents are evaporated at reduced pressure and the residue is redissolved in methanol/water (95:5, 300 ml). After addition of $NaN_3$ (18.2 g, 0.28 mol) the solution is boiled for 18 h under reflux. Solvent is then evaporated under reduced pressure and the residue is partitioned between ether and saturated brine. Chromatography of the residue of the dried ($Na_2SO_4$) organic phase on silica gel (260 g), eluting with hexane/ethyl acetate (2:1) gives 1,8-diazido-3,6-dioxa-octane 19.

(b) To a solution of diazide 19 (14.67 g, 0.073 mol) in THF (100 ml) 1.5 g of 5% Pt on charcoal is added. The mixture is stirred for 12 h under hydrogen. Filtration through Celite™ and evaporation of solvents at reduced pressure gives 1,8-diamino-3,6-dioxa-octane 20.

(c) To a solution of 20 (1.0 g, 6.76 mmol) in pyridine (5 ml) a solution of diphenyl-(4-methoxyphenyl)-methyl chloride (2.09 g, 6.76 mmol) in pyridine (10 ml) is added at 5° C. within 5 min. After stirring for 3 h at 0° C. solvent is evaporated under reduced pressure at 20° C. The residue is partitioned between ethyl acetate and saturated brine. The organic phase is separated, dried ($Na_2SO_4$) and solvent is evaporated. Chromatography (170 g of silica gel) of the residue (3.1 g) eluting with chloroform/methanol/water (65:25:4) yields 8-[N-di-phenyl-(4-methoxyphenyl)-methyl]-amino-3,6-dioxa-octylamine 21.

(d) A solution of 21 (395 mg, 0.94 mmol), γ-butyrolacton (0.81 ml, 9.4 mmol), and triethylamine (1.31 ml, 9.4 mmol) in dry, oxygen-free methanol (17 ml) is boiled for 18 h under reflux. Solvents are removed under reduced pressure and the residue (635 mg) is chromatographed on silica gel (100 g). Elution with ethyl acetate gives A7. $^1$H-NMR (400 MHz, $CDCl_3$): 1.33 (t, J=7, SH); 1.90 (quint., J=7, NH—CO—$CH_2CH_2CH_2SH$); 2.1 (broad, NH); 2.20 (t, J=7, NH—CO—$CH_2(CH_2)_2SH$); 2.39 (t, J=6, $CH_2NH$); 2.53 (q, J=7, $CH_2SH$); 3.43 (m, $CH_2NH$—CO); 3.5–3.67 (m, 4 $OCH_2$); 3.80 (s, $OCH_3$); 6.02 (broad, NH); 6.78–6.88 (2H), 7.15–7.25 (2H), 7.25–7.33 (4H), 7.35–7.45 (2H), 7.45–7.55 (4H) (arom. CH). MS(EI): 523 $(M+H)^+$.

B Preparation of Activated Polyamide Derivatives

EXAMPLE B1

Preparation of N(6)-chloroacetyl-poly-L-lysines B1a, B1b and B1c

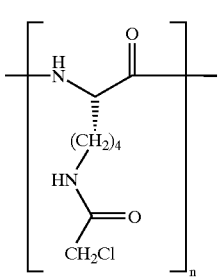

(B1)

(a) 500 mg (2.39 mmol eq) of poly-L-lysine hydrobromide (M: 30,000–70,000) are suspended in 8 ml of DMF under argon. The suspension is cooled down to 0° C. and 2.5 ml of 2,6-lutidine are added. A solution of 1 g (5.85 mmol) of chloroacetic anhydride in 4 ml of DMF is added dropwise within 15 min. The mixture is subsequently heated slowly to RT and stirred for 5 h. The faintly yellow, slightly turbid solution is added dropwise to 100 ml of diethyl ether/ethanol (2:1) with the formation of a colourless precipitate. Following filtration (through a sintered-glass filter initially without applying a vacuum) washing takes place with ethanol, water, with ethanol again and finally with diethylether. The crude product is dissolved in as little DMF as possible and precipitated once again in diethyl ether/ethanol. After drying in vacuo at RT B1a [M: 30,000–70,000 (n=250)] is obtained. $^1$H-NMR (DMSO, 500 MHz) δ=8.20 (2H, s, 2×N$\underline{H}$); 4.05 (2H, s, —CO—C$\underline{H}_2$—Cl); 3.80 (1H, s, C$\underline{H}$); 3.05 (2H, s, —C$\underline{H}_2$—NH—CO—); 2.00–1.20 (6H, m, —CH—(C$\underline{H}_2)_3$—$CH_2$—NH—).

(b) In an analogous manner N(6)-chloroacetyl-poly-L-lysine B1b [M: 4,000–15,000 (n=50)] is obtained from 50 mg (0.24 mmol eq) of poly-L-lysine hydrobromide (M: 4,000–15,000) and N(6)-chloroacetyl-poly-L-lysine B1c [M: 150,000–300,000 (n=1050)] is obtained from 50 mg (0.24 mmol) of poly-L-lysine hydrobromide (M: 150,000–300,000). The $^1$H-NMR spectra are identical to that of compound B1a.

EXAMPLE B2

Synthesis of N(6)-chloroacetyl-poly-D-lysines B2a, B2b and B2c (a) In analogy to Example B1(a) N(6)-chloroacetyl-poly-D-lysine B2a [M: 30,000–70,000 (n=250)] is obtained from 100 mg (0.48 mmol eq) of poly-D-lysine hydrobromide (M: 30,000–70,000), and N(6)-chloroacetyl-poly-D-lysine B2b [M: 4,000–15,000 (n=50)] from 250 mg (1.196 mmol eq) of poly-D-lysine hydrobromide (M: 4,000–15,000). The $^1$H-NMR spectra are identical to those of compounds B1a and B1b, respectively.

(b) A solution of poly-D-lysine hydrobromide (478 mg, 2.29 mmol eq; M: 150,000–300,000) in water (50 ml) is passed through a column (2 cm diameter, length 11 cm) filled with basic ion-exchange resin (Dowex® 1×8, 20–50 mesh, OH-form). Elution with water until the pH reaches 7 is followed by neutralisation with 10% aqueous p-toluene-sulfonic acid to pH 3. After lyophilisation of the eluate the residue is dissolved in DMF (10 ml) and 2,6-lutidine as well as a solution of chloroacetic anhydride (800 mg) in DMF (2 ml) are added at 0° C. After stirring at 0° C. for 18 h under argon, the mixture is diluted with ethanol (100 ml) and the product is precipitated by the addition of diethyl ether (250 ml). The precipitate, collected by gravity filtration, is redissolved in DMF (20 ml), and the solution is then added within 10 min to ethanol (80 ml). The resulting suspension is stirred for 16 h at RT before diethylether (300 ml) is added within 20 min. Filtration and drying of the precipitate at reduced pressure (high vacuum) affords B2c [M: 150,000–300,000 (n=1000)]. The $^1$H-NMR spectrum is identical to that of compound B1c.

EXAMPLE B3

Synthesis of N(6)-chloroacetyl-poly-D/L-lysines B3a, B3b and B3c (a) 250 mg (1.19 mmol eq) of poly-D/L-lysine hydrobromide (M: 30,000–70,000) are suspended in 4 ml of DMF under argon. The suspension is cooled down to 0° C. and 1.25 ml of 2,6-lutidine are added. A solution of 500 mg (2.93 mmol) of chloroacetic anhydride in 2 ml of DMF is added dropwise within 15 min. The mixture is subsequently heated slowly to RT and stirred for 16 h. The working-up and purification take place in analogy with Example B1(a) to obtain B3a [M: 30,000–70,000 (n=250)]. $^1$H-NMR (DMSO, 500 MHz) δ=8.20 (1H, s, N(6)H); 8.05 and 7.90 (in each case 1/2H, 2s, N(2)H); 4.25 (1H, s (br), CH); 4.05 (2H, s, —CO—CH$_2$—Cl); 3.05 (2H, s, —CH$_2$—NH—CO—); 1.70–1.20 (6H, m, —CH—(CH$_2$)$_3$—CH$_2$—NH—).

(b) In an analogous manner N(6)-chloroacetyl-poly-L-lysine B3b [M: 4,000–15,000 (n=50)] is obtained from 50 mg (0.24 mmol eq) of poly-D/L-lysine hydrobromide (M: 4,000–15,000), and N(6)-chloroacetyl-poly-L-lysine B3c [M: 150,000–300,000 (n=1050)] from 500 mg (2.392 mmol eq) of poly-L-lysine hydrobromide (M: 150,000–300,000). The $^1$H-NMR spectra are identical to that of compound B3a.

EXAMPLE C1

Preparation of Conjugates Type I (i) Starting from poly-N(6)-chloroacetyl-L-lysine (a) B1a (10 mg, 0.0489 mmol eq) and thiol A2 (10.3 mg, 0.0147 mmol) are dissolved, in succession, in 2.0 ml dry and oxygen-free DMF at RT and under argon. DBU (7.3 μl, 0.0489 mmol) is added to the clear solution. After stirring at RT for 1 h thioglycerol (12.7 μl, 0.147 mmol) and triethylamine (33.4 μl 0.24 mmol) are added and stirring is continued for 18 h. The colorless solution is added dropwise to 15 ml of diethyl ether/ethanol (1:1). The precipitate formed is separated by filtration through a fritted funnel by gravity, washed with ether/ethanol (1:1), dissolved in water, and the resulting solution subjected to ultrafiltration using an Amicon apparatus equipped with a YM-3 membrane (MW 3000 cutoff). Washing is done with five 10 ml portions of ultrapure water. Lyophilisation of the contents of the filter chamber taken up in water affords C1a [x=0.25 (n=250)] with 25% of saccharide derivatisation (x=0.25) according to $^1$H-NMR (integration of selected signals). $^1$H-NMR(500 MHz, D$_2$O), selected signals: 2.26–2.36 (m, NH—CO—CH$_2$CH$_2$CH$_2$S, A2); 2.53–2.58 (m, NH—CO—CH$_2$CH$_2$CH$_2$S, A2); 2.58–2.68 and 2.7–2.8 (2m, SCH$_2$—CHOH—CH$_2$OH); 4.49 and 4.51 (2d, J=8, H—C(1), H—C(1'), A2); 5.12 (d, J=4, H—C(1"), A2).

B1a is treated with varying amounts of A2, A3, A4 or A8 and thioglycerol as described above giving conjugates Type I of varying saccharide derivatisation according to $^1$H-NMR (integration).

| conjugates Type I (n = 250) | amount of B1a | amount of A2, A3, A4 or A8 | % of saccharide derivatisation |
|---|---|---|---|
| C1b | 10 mg, 48.9 μmol eq | A2: 3.44 mg, 4.89 μmol | 8% (x = 0.08) |
| C1c | 10 mg, 48.9 μmol eq | A2: 6.89 mg, 9.78 μmol | 16% (x = 0.16) |
| C1d | 10 mg, 48.9 μmol eq | A2: 17.2 mg, 24.5 μmol | 41% (x = 0.41) |
| C1e | 10 mg, 48.9 μmol eq | A2: 24.1 mg, 34.2 μmol | 61% (x = 0.61) |

| conjugates Type I (n = 250) | amount of B1a | amount of A2, A3, A4 or A8 | % of saccharide derivatisation |
|---|---|---|---|
| C4 | 20 mg, 97.8 μmol eq | A3: 19.5 mg, 29.3 μmol) | 23% (x = 0.23) |
| C5 | 30 mg, 146.7 μmol eq | A4: 23.9 mg, 44 μmol) | 25% (x = 0.25) |
| C1k | 10 mg, 48.9 μmol eq | A8: 12.6 mg, 12 μmol) | 22% (x = 0.22) |

(b) In analogy to (a) starting from B1b (20 mg, 97.8 μmol eq), A2 (20.7 mg, 29.3 μmol) and thioglycerol affords C1f (n=50) saccharide derivatisation: 28% (x=0.28).

(c) B1c is treated with varying amounts of A2, A4 or A8 and thioglycerol as described above giving conjugates Type I of varying saccharide derivatisation according to $^1$H-NMR (integration).

| conjugates Type I (n = 1050) | amount of B1c | amount of A2, A4 or A8 | % of saccharide derivatisation |
|---|---|---|---|
| C1g | 10 mg, 48.9 µmol eq | A2: 10.3 mg, 14.7 µmol | 28% (x = 0.28) |
| C1h | 20 mg, 97.8 µmol eq | A4: 14.3 mg, 26.4 µmol | 21% (x = 0.21) |
| C1i | 20 mg, 97.8 µmol eq | A8: 25.1 mg, 24 µmol | 25% (x = 0.25) |
| C1j | 70 mg, 342 µmol eq | A2: 24.1 mg, 34.2 µmol | 9% (x = 0.09) |
|  |  | A8: 35.2 mg, 34.2 µmol | 9% (x = 0.09) |
|  |  | A4: 18.6 mg, 34.2 µmol | 9% (x = 0.09) |

(ii) (a) Starting from poly-N(6)-chloroacetyl-D-lysine: B2a (10 mg, 48.9 µmol eq) is treated with A2 (10.3 mg, 14.7 µmol) and thioglycerol as described in example C1(I)a. Filtration of the contents of the ultrafiltration chamber through an Acrodisc™ and lyophilisation of the filtrate gives C2 [x=0.35 (n=250)] with 35% of saccharide derivatisation (x=0.35) according to $^1$H-NMR (integration).

(b) In analogy to (a) starting from B2c (100 mg, 489 µmol eq), A2 (86 mg, 122 µmol) and thioglycerol affords C2b (n=1000), saccharide derivatisation: 24% (x=0.24).

(iii) Starting from poly-N(6)-chloroacetyl-D,L-lysine: B3a (10 mg, 0.0489 mmol eq) is treated with A2 (10.3 mg, 0.0147 mmol) and thioglycerol as described in example C1(I)a giving C3 [x=0.22 (n=250)] with 22% of saccharide derivatisation (x=0.22) according to $^1$H-NMR (integration).

EXAMPLE C2

Preparation of Precursors of Conjugates Type II (i) Precursors of conjugates Type II wherein —Y—R$^{o3}$ is a group of formula Vc (derived from A2, tri)

(a) Poly-N(6)-chloroacetyl-L-lysine (B1a, 200 mg, 978 µmol eq), thiol A2 (172 mg, 244 µmol) and thiol A7 (15.3 mg, 29.3 µmol) are dissolved in dry, oxygen-free DMF (20 ml). DBU (146 µl, 0.978 mmol) is added to the clear solution. After stirring for 40 min at RT and under argon thioglycerol (254 µl, 2.934 mmol) and triethylamine (682 µl, 4.89 mmol) are added and stirring is continued for 18 h. The colorless solution is added to 100 ml of ethanol and diethylether (200 ml) is added dropwise under stirring. The precipitate formed is separated by filtration through a fritted funnel by gravity, washed with ethanol/ether (1:2, 3×30 ml) and dissolved in water. The solution is subjected to ultrafiltration using an Amicon apparatus equipped with a YM-3 membrane (MW=3000 cutoff). Lyophilisation of the contents of the filter chamber taken up in water affords C6a1 [x=0.25, y=0.03 (n=250)].

(b) To a solution of C6a1 (366 mg) in water (25 ml) trichloroacetic acid (1.2 g) is added at 0° C. After stirring for 2 h at 0° C. the solution is neutralized with 2 N sodium hydroxide to pH 11 and subjected to ultrafiltration using an Amicon apparatus equipped with a YM-10 membrane (MW=10000 cutoff). Washing is done with three portions of ultrapure water. After addition of 2 N NaOH (10 drops) to the filter chamber, washing with water is continued (six portions). Lyophilisation of the contents of the filter chamber taken up in water affords C6b1 [x=0.25, y=0.02 (n=250)] with 25% saccharide derivatisation (x=0.25) according to $^1$H-NMR (integration of selected signals), and 2% amine derivatisation (y=0.02) based on the NMR-analysis of C6a1 and the absence of monomethoxy-trityl signals in the $^1$H-NMR of C6b1: 1H-NMR (500 MHz, D$_2$O, 60° C.), selected signals: 2.65–2.75 (m, NH—CO—CH$_2$(CH$_2$)$_2$S, R$_1$, R$_2$); 2.95–3.01 (m, NH—CO—(CH$_2$)$_2$ CH$_2$S, R$_1$, R$_2$); 3.01–3.08 and 3.13–3.19 (2m, HOCH$_2$—CHOH—CH$_2$S, R$_3$); 4.87–4.95 (m, H—C(1), H—C(1'), R$_1$); 5.52 (m, H—C(1"), R$_1$).

Poly-N(6)-chloroacetyl-L-lysine of different polymerisation degree is each treated with thioglycerol and varying amounts of A7 and A2 as described above giving C6bII, C6bIII and C6bIV of varying saccharide and amine derivatisation according to, $^1$H-NMR (integration).

| precursors of conjugates Type II | amount of poly-N(6)-chloro-acetyl-L-lysine | amount of A2 | amount of A7 | % of saccharide derivatisation | % of amine functions |
|---|---|---|---|---|---|
| C6bII (n = 1050) | B1c: 100 mg, 489 µmol eq | 51.6 mg, 73.4 µmol | 7.66 mg, 14.7 µmol | 13 % (x = 0.13) | 2.6 % (y = 0.026) |
| C6bIII (n = 250) | B1a: 100 mg, 489 µmol eq | 51.6 mg, 73.4 µmol | 7.66 mg, 14.7 µmol | 14 % (x = 0.14) | 2.6% (y = 0.026) |
| C6bIV (n = 50) | B1b: 150 mg, 733.5 µmol eq) | 129.1 mg, 183.4 µmol | 19.1 mg, 36.67 µmol | 23 % (x = 0.23) | 3 % (y = 0.03) |

(ii) Precursors of conjugates Type II wherein —Y—R$^{o3}$ is a group of formula Vb (derived from A4, di), Va (derived from A6, mono), Vf (derived from A8, penta) or Ve (derived from A10, penta)

Poly-N(6)-chloroacetyl-L-lysine is treated with thioglycerol and varying amounts of A7 and A4, A6, A8 or A10 as described above (example C21) giving C7a, C7b, C8b1, C9b1 and C10b1 of varying saccharide and amine derivatisation according to $^1$H-NMR (integration).

| Precursor of conjugates Type II | amount of poly-N(6)-chloro-acetyl-L-lysine | amount of thiol A6, A4, A8 or A10 | amount of A7 | % of saccharide derivatisation | % of amine functions |
|---|---|---|---|---|---|
| C7a (n = 160) | B1: 70 mg, 342 µmol eq | A6: 26 mg, 68.5 µmol | 5.36 mg, 10.3 µmol | 20 % (x = 0.20) | 3 % (y = 0.03) |
| C7b (n = 250) | B1a: 111 mg, 54.3 µmol eq | A6: 50mg, 109 µmol | 8.6 mg, 16.4 µmol | 21.5 % (x = 0.215) | 2 % (y = 0.02) |
| C8b (n = 1050) | B1c: 130 mg, 635.7 µmol eq | A4: 51.9mg, 95.6 µmol | 10.0 mg, 19.1 µmol | 16 % (x = 0.16) | 2.5 % (y = 0.025) |
| C9b (n = 1050) | B1c: 99.7 mg, 488 µmol eq | A8: 75.1 mg, 73.1 µmol | 7.6 mg, 14.6 µmol | 12.5 % (x = 0.125) | 2.5 % (y = 0.025) |
| C10b (n = 1050) | B1c: 500 mg, 2.44 µmol eq | A10: 376 mg, 366 µmol | 38.2 mg, 73.2 µmol | 16 % (x = 0.16) | 2.5 % (y = 0.025) |

D Preparation of Conjugates Type II

EXAMPLE D1

Conjugates Type II Comprising CH-Sepharose 4B (a) C6bI: 4.0 g NHS-activated CH-Sepharose 4B (Pharmacia Biotech) are washed with 1 mM HCl (800 ml on a fritted funnel (15 min) and added to a solution of C6bl (20 mg) in $NaHCO_3$-buffer (0.1 M, 0.5 M in NaCl, pH 8, 6 ml). After shaking for 2 h at RT the buffer is separated by gravity filtration and the resin is washed with $NaHCO_3$-buffer (0.1 M, 0.5 M in NaCl, pH 8, 3 times 50 ml) before treatment with 1 M ethanolamine (pH 8) for 1 h at RT. Filtration and washing with water (3 times 20 ml), TRIS-buffer (0.1 M, 0.5 M in NaCl, pH 8, 30 ml), acetate buffer (0.1 M, 0.5 M in NaCl, pH 4, 30 ml)—3 times alternating—, and 20% ethanol (3 times 50 ml) gives D1a with 5 µmol of carbohydrate epitope per ml of resin stored in 20% ethanol.

(b) C7a: 1.0 g NHS-activated CH Sepharose 4B is treated as above (example D1a) with a solution of C7a (25 mg) in 0.1 M $NaHCO_3$ (0.5 M NaCl, pH 8, 6 ml) affording D1b with 4 µmol of carbohydrate epitope per ml of resin stored in 20% ethanol.

EXAMPLE D2

Conjugates Type II Comprising Sepharose 4 Fast Flow 11 ml Sepharose 4 fast flow suspended in 2-propanol are washed with cold (0° C.) 1 mM HCl (6 times 20 ml) and transferred with cold (0° C.) $NaHCO_3$-buffer (0.1 M, 0.05 M in NaCl, pH 8, 1.5 ml) to a solution of precursor C6bl (150 mg) in 6 ml $NaHCO_3$-buffer (0.1 M, 0.05 M in NaCl, pH 8, 6 ml) at 0° C. After shaking for 3 h at RT the mixture is filtered and the resin is washed with water (50 ml) before being suspended in 1 M ethanolamine (pH 8, 20 ml) and shaken at RT for 15 h. The resin is separated by filtration and washed alternately with TRIS-buffer (0.1 M, 0.5 M in NaCl, pH 8, 30 ml) and acetate buffer (0.1 M, 0.5 M in NaCl, pH 4, 30 ml) three times affording D2a with 5 µmol of carbohydrate epitope per ml of resin stored in 20% ethanol.

According to the above procedure conjugates Type II D2b, D3, D5, D6, D7 and D8 are prepared:

| conjugate Type II | amount of sepharose | precursor in 1 ml 0.1 M $NaHCO_3$ (0.5 M NaCl, pH 8) | sugar epitopes per ml resin |
|---|---|---|---|
| D2b | 11 ml | C6bII (146 mg) | 3.9 µmol |
| D3 | 11 ml | C6bIII (141.5 mg) | 3.9 µmol |
| D5 | 2 ml | C7b (24.8 mg) | 7 µmol |
| D6 | 11 ml | C8b (140 mg) | 4.7 µmol |
| D7 | 11 ml | C9b (165 mg) | 2.9 µmol |
| D8 | 50 ml | C10b (800 mg) | 3 µmol |

E Biological Activity of the Compounds

EXAMPLE E1

Binding Affinities of Conjugates Type I

Nunc Polysorp plates (catalog #475094) are coated overnight at 4° C. with 0.1 m/well of a 5 µg/ml solution of C1g (→C1g-ELISA) or C1h (→C1h-ELISA) or C11 (→C1-ELISA) in PBS. Plates are blocked with 0.250 ml/well of a 10% solution of SEA BLOCK (Pierce, catalog #37527) for 24 h at 4° C. The plates are washed 3 times with 0.250 ml of PBS containing 0.02% Tween 20.

Pooled human serum (Sigma H-1513) is diluted 1:20 in PBS buffer containing 0.1% Tween 20 and 10% Blocker BSA (Pierce catalog #37525). A 60 µl aliquot of the human serum dilution is placed in low-bind U shaped wells and 60 µl of a serial dilution of the conjugate Type I is added in successive wells at the appropriate series of concentrations.

After 1 h incubation at RT 0.100 ml of the serum mixture is transferred on to the washed polymer-coated wells. The plates are incubated for 1 h at RT and washed 3 times with PBS containing 0.02% Tween 20. The plates are then filled with 0.100 ml of a 1:2500 dilution of an anti human IgG-peroxidase conjugate (Jackson Immunoresearch 109-036-098) or, alternatively, with an anti human IgM-peroxidase conjugate (Jackson Immunoresearch 109-036-129) in PBS containing 10% Blocker BSA and 0.1% Tween 20. The plates are incubated for 1 h at RT and then washed 5 times with PBS containing 0.02% Tween 20. The plates are developed with 0.100 ml of TMB substrate (Sigma catalog #T-3405) and stopped after 10 min of substrate development with 50 µl of 2 M $H_2SO_4$. Absorbance is read at 450–650 nm using a microtiter plate reader. For the analysis absorbance values are plotted against conjugate concentrations. Linear B trisaccharide (Dextra catalog #GN334) is used as a standard for measuring relative $IC_{50}$.

TABLE 1

Binding affinities of conjugates Type I
as measured with C1g-coated plates
Affinities are tabulated as relative binding affinities
($RIC_{50}$ = $IC_{50}$ Linear B/$IC_{50}$ compound)

| Compound | $RIC_{50}$ IgG | $RIC_{50}$ IgM | Compound | $RIC_{50}$ IgG | $RIC_{50}$ IgM |
|---|---|---|---|---|---|
| C1b | .0070 | .0134 | C2 | .0007 | .0026 |
| C1c | .0017 | .0066 | C3 | .0004 | .0013 |
| C1a | .0018 | .0040 | C4 | .004 | .013 |
| C1d | .003 | .133 | C1g | .0004 | .0001 |
| C1e | .007 | >.3 | C1f | .002 | .07 |
| C5 | .18 | .009 | | | |

EXAMPLE E2

Xenoantibody Removal from Cynomolgus Monkeys

A group of 4 cynomolgous monkeys (average weight 3 kg) are injected with a 1 mg/kg dose of conjugate Type I at 0, 72 and 168 h. The animals are bled at various intervals and the serum is assayed for anti-αGal antibodies by ELISA against C1g (Example E1). A single dose of conjugate Type I provokes a sharp decrease in antibody titer, followed by a recovery of antibody titer to a value below the starting titer. By a second and particularly a third dose recovery of antibody titer is effectively stopped for a long period of time.

TABLE 3

Antibody titers in cynomolgus monkeys receiving injections of C1g
Results are tabulated as titers relative to a standard human serum.

| Time (h) | Animal 1 | | Animal 2 | | Animal 3 | | Animal 4 | |
|---|---|---|---|---|---|---|---|---|
| | IgG | IgM | IgG | IgM | IgG | IgM | IgG | IgM |
| 0 | 1.6 | 0 | 0.85 | 0.95 | 1.5 | 0.17 | 0.24 | 3 |
| 1 | 0 | 0 | 0 | 0.11 | 0 | 0 | 0 | 0.07 |
| 72 | 0.31 | 0 | 0.35 | 0.08 | 0.16 | 0 | 0.06 | 0.32 |
| 73 | 0 | 0 | 0 | 0 | 0 | 0 | 0 | 0.01 |
| 168 | 0.21 | 0 | 0.4 | 0.34 | 0.29 | 0.05 | 0.03 | 0.95 |
| 169 | 0 | 0 | 0 | 0 | 0 | 0 | 0 | 0.13 |
| 264 | 0.18 | 0 | 0.1 | 0.41 | 0.06 | 0.12 | 0.06 | 0.84 |
| 672 | 0.73 | 0 | 0.45 | 0.51 | 0.44 | 0.38 | 0.23 | 1.55 |

EXAMPLE E3

Measurement of Antibody Titers

Nunc Polysorp plates (catalog #475094) are coated overnight at 4° C. with 0.1 ml/well of a 5 μg/ml solution of C1g or C1h or C11 in PBS. Plates are blocked with 0.250 ml/well of a 10% solution of SEA BLOCK (Pierce, catalog #37527) for 24 h at 4° C. The plates are washed 3 times with 0.250 ml of PBS containing 0.02% Tween 20. An 0.100 ml aliquot of the serum sample is added to the wells is successive dilutions. Typically the dilutions are as follows 1:5; 1:15; 1:45; 1:135; 1:405; 1:1215; 1:3645; 1:10935 etc. The diluent is PBS buffer containing 0.1% Tween 20 and 10% SEABLOCK. The plates are incubated for 1 h at RT and washed three times with PBS containing 0.02% Tween 20. The plates are then filled with 0.100 ml of a 1:2500 dilution of an anti human IgG-peroxidase conjugate (Jackson Immunoresearch 109-036-098) or, alternatively, with an anti human IgM-peroxidase conjugate (Jackson Immunoresearch 109-036-129) in PBS containing 10% Blocker BSA and 0.1% Tween 20. The plates are incubated for 1 h at RT and then washed 5 times with PBS containing 0.02% Tween 20. The plates are developed with 0.100 ml of TMB substrate (Sigma catalog #T-3405) and stopped after 10 min of substrate development with 50 μl of 2 M $H_2SO_4$. Absorbance is read at 450–650 nm using a microtiter plate reader. For the analysis absorbance values are plotted against the log of dilution factor and the titer is found by extrapolating the linear portion of the curve to the X axis. A standard serum is used whose titer is normalized to 1.

EXAMPLE E4

Immunoaffinity Chromatography of Human Serum 5 ml of immobilized conjugate Type II is packed in a column (1×3.5 cm). Pooled human serum (Sigma H-1513, filtered through a 0.4 μm filter) is passed through the column by pumping at a flow rate of 4 ml/min. Fractions of 10 ml each are collected after the column. Fractions are assayed for the presence of anti Galα1,3Gal xenoreactive antibodies using an ELISA assay as described in Example E3 above. Using the material from Example D2 at least 200 ml of pooled human blood serum per ml gel is cleaned in a single pass.

EXAMPLE E5

Comparison of Binding Affinity and Antibody Specificity of D2b, D6 and D7

A volume of 200 ml serum is passed through a first column filled with D6 and tested in ELISA assays (according to Example E3). The serum is subsequently passed through a second column filled with D2b, tested, and then passed through a third column filled with D7 and tested by ELISA again. Samples after each column are assayed. Each of the columns tested is most efficient in removing antibodies against the type of oligosaccharide it carries. Thus D6 is efficient in removing disaccharide binding antibodies, D2b removes the trisaccharide binding antibodies and D7 removes the pentasaccharide binding antibodies. Serum passed through two columns is depleted from antibodies against the two epitopes carried by these columns, but retains antibodies against the third epitope. Serum passed from all three columns is depleted from antibodies against all three saccharides.

EXAMPLE E6

Binding Affinity and Antibody Specificity of Mixed Bed Column 2 ml of D6, 2 ml of D2b and 1 ml of D7 are mixed. The material is packed into a 5 ml column and 200 ml of human serum is passed through. Fractions are 10 ml each. Every second fraction collected is assayed. Fractions are assayed by ELISA to all three α-galactosylated antigens and also for cytotoxicity towards PK1 cells. The mixed-bed column efficiently removes anti-αGal activity from serum as measured by the three ELISA assays described in Example E3.

EXAMPLE E7

Antibody Binding to Pig Cells

Serum samples after passage from each column (Example E5) are assayed for binding to pig PK15 cells (ATCC #CCL-33). Cells are trypsinized and 1×10⁶ cells are suspended in 0.3 ml of PBS/0.1% BSA. The cells are incubated with 0.040 ml of serum sample (pretreated for 10 min at 56° C.) for 30 min in ice. The cells are brought up in 3 ml PBS, centrifuged and resuspended in 0.3 ml PBS 0.1% BSA. An aliquot of 0.004 ml of a secondary antibody (anti hIgG/FITC Jackson Immunoresearch #109-096-098 or anti hIgM/FITC Jackson ImmunoResearch #109-096-129) is added and incubated for 30 min in ice. After washing once in PBS the cells are analyzed by FACS. The mean fluorescence of pooled human serum is 480, of serum after D6 column (Example E5) is 117, of serum after D6 and D2b columns (Example E5) is 80, of serum after D6, D2b and D7 columns (Example E5) is 54 and of serum after mixed bed column (Example E6) is 52 (all obtained with the anti hIgG antibody). Similar results are obtained with the anti hIgM measurements.

EXAMPLE E8:

Immunoapheresis of Anti-αGal Antibodies in Baboons

A volume of 7 ml D6, 7 ml D2b and 5 ml D7 is combined with 45 ml Sepharose CL2B (Pharmacia) to make an immunoapheresis column. The column is used with a Citem 10 immunoapheresis system (Excorim) to remove anti-αGal antibodies from 2 baboons (6 kg weight). After passage of 600 ml and 500 ml respectively through the column (ca. 2 blood volumes) the anti-αGal antibody titers drop to 10% of the initial levels (as measured by an ELISA against C1g, Example E3).

What is claimed is:

1. A polyamide conjugate comprising either (a) an oligosaccharide terminating with an alpha-linked D-galactopyranose or N-glycol-neuraminic acid at its reducing end; or (b) cellulose, agarose, or sepharose, bound to a linear polyamide backbone, wherein the polyamide backbone comprises at least one structural element of formula I

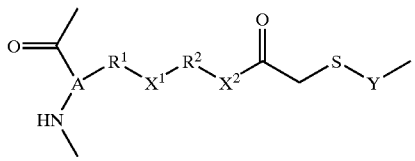

(I)

and in case (b) additionally at least one structural element of formula II

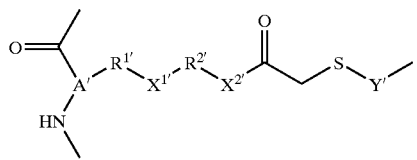

(II)

wherein
each of A and A', independently, is a trivalent bridging group;
each of $R^1$ and $R^{1'}$, independently, is a direct bond or $C_1$–$C_6$ alkylene;
each of $X^1$ and $X^{1'}$, independently, is —C(O)O—, —C(O)NR—, —NR—, —S—, or —O—.
each of $R^2$ and $R^{2'}$, independently, is a direct bond or a bivalent bridging group;
each of $X^2$ and $X^{2'}$, independently, is a direct bond or —O— or —NR—; wherein R is hydrogen, OH, $C_1$–$C_{12}$alkyl, $C_2$–$C_{12}$alkenyl, $C_3$–$C_8$cycloalkyl, $C_3$–$C_8$cycloalkenyl, $C_2$–$C_7$heterocycloalkyl, $C_2$–$C_{11}$heterocycloalkenyl, $C_6$ or $C_{10}$aryl, $C_5$–$C_9$heteroaryl, $C_7$–$C_{16}$aralkyl, $C_8$–$C_{16}$aralkenyl with $C_2$–$C_6$alkenylene and $C_6$ or $C_{10}$aryl, or di-$C_6$ or $C_{10}$aryl-$C_1$–$C_6$-alkyl; and
each of Y and Y', independently, is a direct bond or a bivalent bridging group;
with the proviso that $X^1$ or $X^{1'}$, is not —NR—, —S— or —O— when $R^1$ or $R^{1'}$ is a direct bond.

2. A polyamide conjugate of claim 1, wherein
(a) the polyamide backbone comprises at least one structural element of formula Iaa,

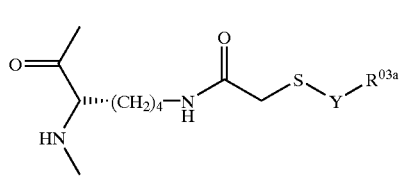

(Iaa)

wherein $R^{03a}$—Y— is a group of formula Va, Vb, Vc, Vd, Ve or Vf

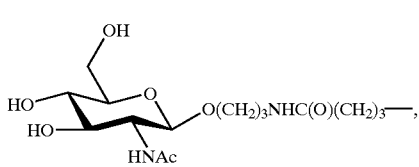

(Va)

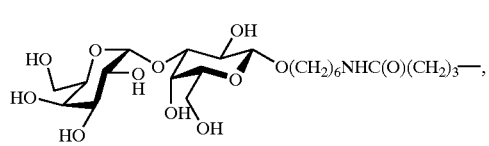

(Vb)

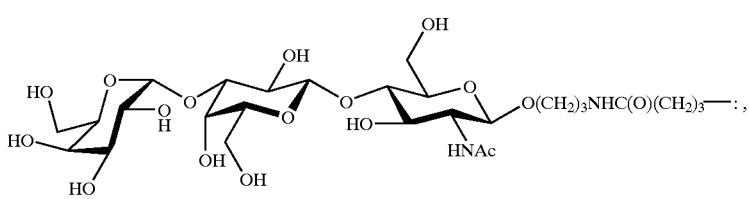

(Vc)

-continued

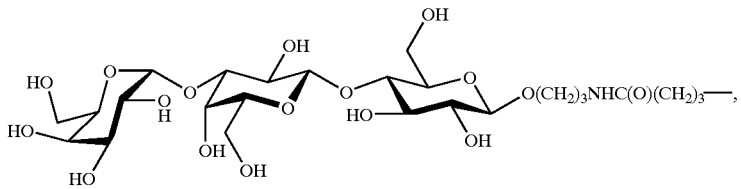
(Vd)

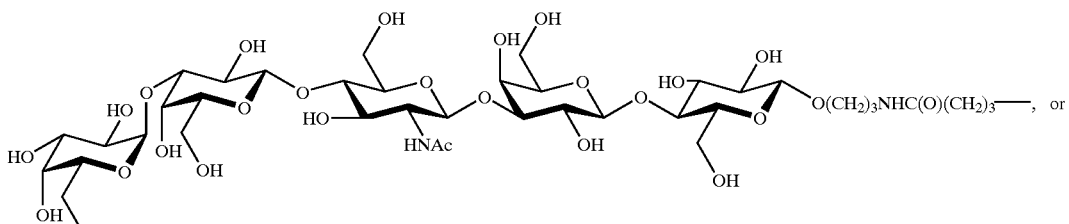
(Ve)

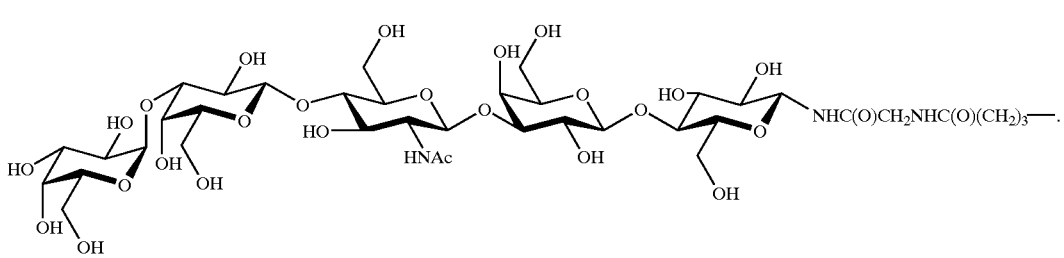
(Vf)

or (b) the polyamide backbone comprises at least one structural element of formula Ia,

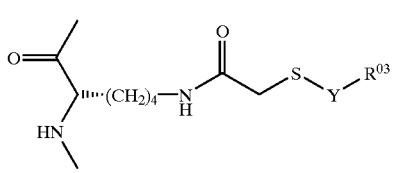
(Ia)

wherein —Y—R$^{03}$ is a group of formula Va, Vb, Vc, Vd, Ve, or Vf;
and at least one structural element of formula IIa,

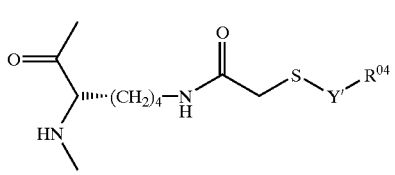
(IIa)

in which —Y'—R$^{04}$ is a group of formula Vg

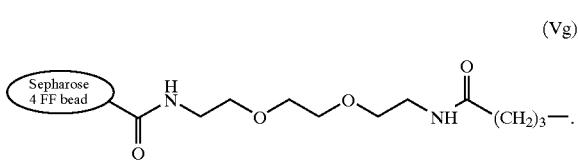
(Vg)

3. A polyamide conjugate of claim 1, wherein the polyamide backbone additionally comprises at least one structural element of formula VIb

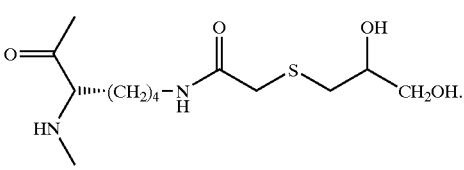
(VIb)

4. A polyamide conjugate of claim 3, wherein the average sum of structural elements [n] is (a) in the range of from 200 to 300 with a polydispersity of from 1.1 to 1.2 and the ratio of structural elements of formula Iaa [x] is 5 to 30%; or in the range of from 900 to 1200 with a polydispersity of from 1.1 to 1.2 and [x] is 5 to 50%; with a ratio of structural elements of formula VIb [z] ranging from 45 to 94%; R$^{03a}$ —Y— being identical or different and selected from groups of formula Va, Vb, Vc, Vd, Ve and Vf; or (b) in the range of from 200 to 300 with a polydispersity of from 1.1 to 1.2, the ratio of structural elements of formula Ia [x] wherein R$^{03}$ —Y— is a group selected from a group consisting of groups of formula Va, Vb, Vc, Vd, Ve and Vf is 5 to 30% and the ratio of structural elements of formula IIb [y]

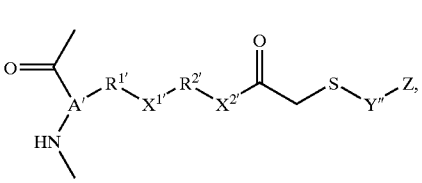
(IIb)

wherein
A' is a trivalent bridging group;
R$^{1'}$ is a direct bond or C$_1$–C$_6$alkylene;

$X^1$ is —C(O)O—, —C(O)NR—, —NR—, —S—, or —O—;

$R^2$ is a direct bond or a bivalent bridging group;

$X^{2'}$ is a direct bond or —O— or —NR—; wherein R is hydrogen, OH, $C_1$–$C_{12}$alkyl, $C_2$–$C_{12}$alkenyl, $C_3$–$C_8$cycloalkyl, $C_3$–$C_8$cycloalkenyl, $C_2$–$C_7$heterocycloalkyl, $C_2$–$C_{11}$heterocycloalkenyl, $C_6$ or $C_{10}$aryl, $C_5$–$C_9$heteroaryl, $C_7$–$C_{16}$aralkyl, $C_8$–$C_{15}$aralkenyl with $C_2$–$C_6$alkenylene and $C_6$ or $C_{10}$aryl, or di-$C_6$ or $C_{10}$aryl-$C_1$–$C_6$-alkyl;

and Z—Y"— is $H_2N[(CH_2)_2O](CH_2)_2NHC(O)(CH_2)_3$—, is from 1 to 5%; or in the range of from 900 to 1200 with a polydispersity of from 1.1 to 1.2, [x] is 5 to 50% and [y] is from 1 to 5%;

wherein from 45 to 94% of the structural elements are of formula VIb [z]

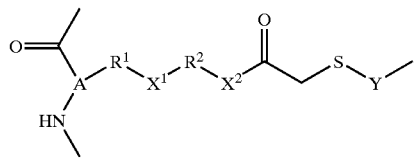

(VIb)

5. An affinity chromatography cartridge comprising as adsorbent a polyamide conjugate of claim 1, comprising cellulose, agarose, or sepharose bound to a polyamide backbone, wherein the polyamide backbone comprises at least one structural element of formula I

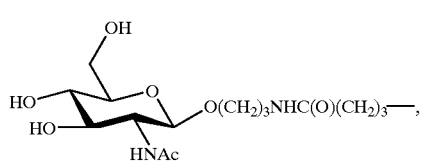

(I)

and at least one structural element of formula II

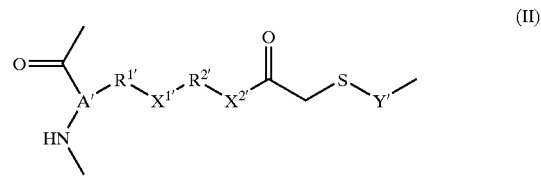

(II)

wherein
each of A and A', independently, is a trivalent bridging group;
each of $R^1$ and $R^{1'}$, independently, is a direct bond or $C_1$–$C_6$alkylene;
each of $X^1$ and $X^{1'}$, independently, is —C(O)O—, —C(O)NR—, —NR—, —S—, or —O—,
each of $R^2$ and $R^{2'}$, independently, is a direct bond or a bivalent bridging group;
each of $X^2$ and $X^{2'}$, independently, is a direct bond or —O— or —NR—; wherein R is hydrogen, OH, $C_1$–$C_{12}$alkyl, $C_2$–$C_{12}$alkenyl, $C_3$–$C_8$cycloalkyl, $C_3$–$C_8$cycloalkenyl, $C_2$–$C_7$heterocycloalkyl, $C_2$–$C_{11}$heterocycloalkenyl, $C_6$ or $C_{10}$aryl, $C_5$–$C_9$heteroaryl, $C_7$–$C_{16}$aralkyl, $C_8$–$C_{16}$aralkenyl with $C_2$–$C_6$alkenylene and $C_6$ or $C_{10}$aryl, or di-$C_6$ or $C_{10}$aryl-$C_1$–$C_6$-alkyl; and
each of Y and Y', independently, is a direct bond or a bivalent bridging group;
with the proviso that $X^1$ or $X^{1'}$ is not —NR—, —S— or —O— when $R^1$ or $R^{1'}$ is a direct bond or a mixture of such polyamide conjugates.

6. A composition comprising a polyamide conjugate of claim 2 wherein the polyamide backbone comprises at least one structural element of formula Iaa,

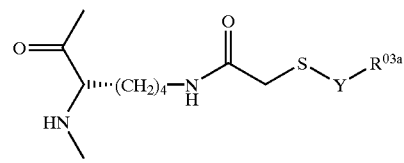

(Iaa)

wherein $R^{03a}$ —Y— is a group of formula Va, Vb, Vc, Vd, Ve, or Vf

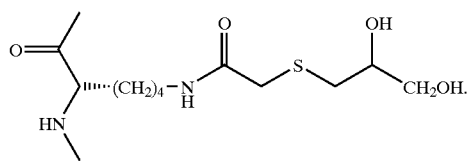

(Va)

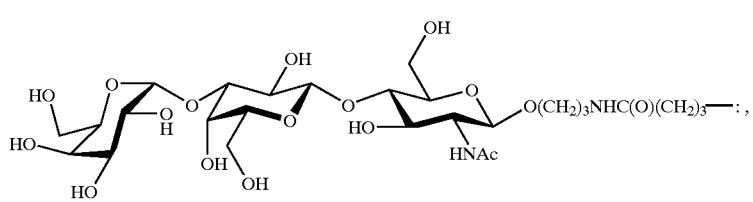

(Vb)

(Vc)

-continued

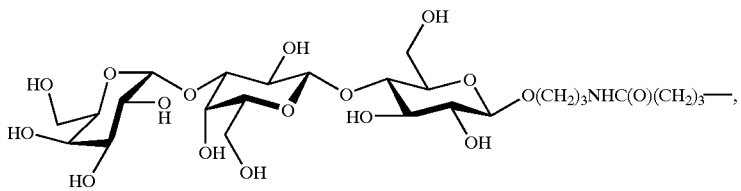
(Vd)

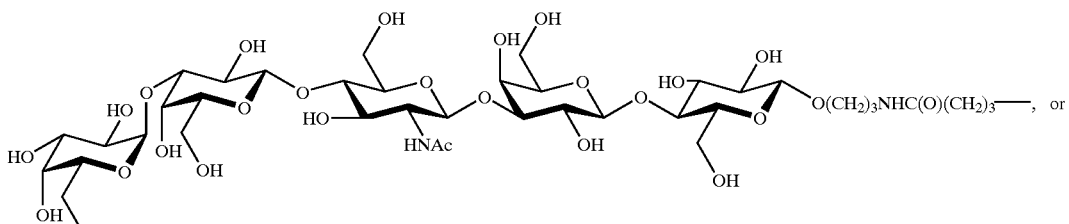
(Ve)

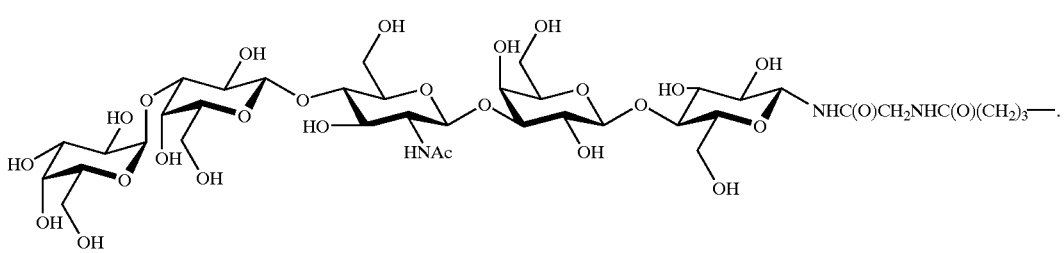
(Vf)

or
(b) the polyamide backbone comprises at least one structural element of formula Ia,

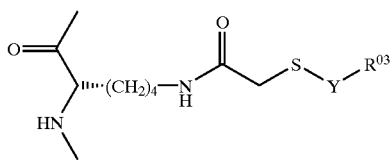
(Ia)

wherein —Y—R$^{03}$ is a group of formula Va, Vb, Vc, Vd, Ve, or Vf;
and at least one structural element of formula IIa,

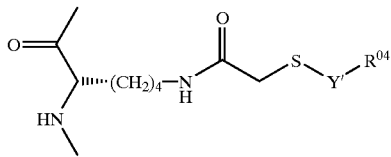
(IIa)

in which —Y'—R$^{04}$ is a group of formula Vg

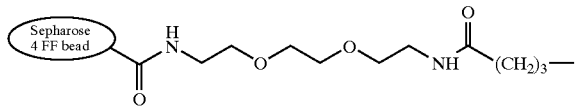
(Vg)

or a mixture of such polyamide conjugates.

7. A composition of claim 6, wherein the polyamide conjugate comprises at least one structural element wherein the oligosaccharide comprises a disaccharide, at least one structural element wherein the oligosaccharide comprises a trisaccharide and at least one structural element wherein the oligosaccharide comprises a pentasaccharide, in a ratio of 1:1:1; or a mixture of polyamide conjugates each conjugate comprising identical oligosaccharides which are a disaccharide, a trisaccharide, or a pentasaccharide, the conjugates being present in the composition in a ratio of 1:1:1.

8. A composition comprising a polyamide conjugate of claim 1, structure 1(a) or a mixture of such polyamide conjugates.

9. The composition of claim 8 wherein the polyamide conjugate comprises at least one structural element wherein the oligosaccharide is derived from a disaccharide, at least one structural element wherein the oligosaccharide is derived from a trisaccharide and at least one structural element wherein the oligosaccharide is derived from a pentasaccharide, in a ratio of 1:1:1; or a mixture of polyamide conjugates each conjugate comprising identical oligosaccharides which are derived from a disaccharide, a trisaccharide, or a pentasaccharide, the conjugates being present in the composition in a ratio of 1:1:1.

10. A composition comprising a polyamide conjugate of claim 1, structure 1(b) or a mixture of such polyamide conjugates.

11. The composition of claim 10 wherein the polyamide conjugate comprises at least one structural element wherein the oligosaccharide is derived from a disaccharide, at least one structural element wherein the oligosaccharide is derived from a trisaccharide, and at least one structural element wherein the oligosaccharide is derived from a pentasaccharide, in a ratio of 1:1:1; or a mixture of polyamide conjugates each conjugate comprising identical oligosaccharides which are derived from a disaccharide, a trisaccharide, or a pentasaccharide, the conjugates being present in the composition in a ratio of 1:1:1.

* * * * *

UNITED STATES PATENT AND TRADEMARK OFFICE
CERTIFICATE OF CORRECTION

PATENT NO. : 6,723,831 B2
DATED : April 20, 2004
INVENTOR(S) : Duthaler et al.

It is certified that error appears in the above-identified patent and that said Letters Patent is hereby corrected as shown below:

<u>Column 44,</u>
Line 13, should read -- each of $R^1$ and $R^{1'}$, independently, is a direct bond or --.
Lines 15-17, should read -- each of $X^1$ and $X^{1'}$, independently, is —C(O)O—, —C(O)NR—, —NR—, —S—, or —O—;
each of $R^2$ and $R^{2'}$, independently, is a direct bond or a --.

<u>Column 47,</u>
Line 3, should read -- $R^{2'}$ is a direct bond or a bivalent bridging group; --.
Line 10, should read -- $C_8$-$C_{16}$aralkenyl with $C_2$-$C_6$alkenylene and $C_6$ or --.

<u>Column 48,</u>
Line 17, should read -- each of $R^2$ and $R^{2'}$, independently, is a direct bond or a --.

Signed and Sealed this

Fourteenth Day of December, 2004

JON W. DUDAS
*Director of the United States Patent and Trademark Office*